United States Patent
Fraga Da Silva et al.

(10) Patent No.: US 11,141,590 B1
(45) Date of Patent: Oct. 12, 2021

(54) ELECTRO-STIMULATION SYSTEMS AND METHODS FOR REHABILITATION AND TREATMENT OF SEXUAL DISORDERS

(71) Applicant: Comphya SA, Lausanne (CH)

(72) Inventors: Rodrigo Araujo Fraga Da Silva, Saint Sulpice (CH); Nikolaos Stergiopulos, Preverenges (CH); Mikael Nils Sturny, Renens (CH)

(73) Assignee: Comphya SA, Lausanne (CH)

( * ) Notice: Subject to any disclaimer, the term of this patent is extended or adjusted under 35 U.S.C. 154(b) by 0 days.

(21) Appl. No.: 17/174,033

(22) Filed: Feb. 11, 2021

(51) Int. Cl.
*A61N 1/36* (2006.01)
*A61N 1/05* (2006.01)

(52) U.S. Cl.
CPC ....... *A61N 1/36107* (2013.01); *A61N 1/0553* (2013.01); *A61N 1/36153* (2013.01);
(Continued)

(58) Field of Classification Search
CPC ............ A61N 1/36107; A61N 1/36153; A61N 1/36175; A61N 1/36192; A61N 1/36157; A61N 1/0553
(Continued)

(56) References Cited

U.S. PATENT DOCUMENTS 3,941,136 A  3/1976 Bucalo
4,585,005 A  4/1986 Lue et al.
(Continued)

FOREIGN PATENT DOCUMENTS

WO  WO-9639932 A1  12/1996
WO  WO-03018113 A1  3/2003
(Continued)

OTHER PUBLICATIONS

Alsaid, et al., Coexistence of adrenergic and cholinergic nerves in the inferior hypogastric plexus: anatomical and immunohistochemical study with 3D reconstruction in human male fetus, J. Anat., 214(5):645-654 (2009).
(Continued)

*Primary Examiner* — Amanda K Hulbert
*Assistant Examiner* — Philip C Edwards
(74) *Attorney, Agent, or Firm* — Eversheds Sutherland (US) LLP; Christopher C. Bolten; Nicola A. Pisano

(57) ABSTRACT

An implantable stimulation system having an implantable stimulation unit coupled to a programmable controller, a stimulation circuit and an array of electrodes disposed on a pair of flexible paddles is provided for selectively stimulating at least one cavernous nerve. The programmable controller is pre-programmed to run an excitation electrode routine that selectively scans the electrode arrays on the paddles with a series of directional current flows, in at least two directions and within at least two regions, to optimize electrode selection for use in stimulating the cavernous nerve. The implantable stimulation system may be programmed to run a first stimulation pulse sequence corresponding to a first mode for invoking a rapid erectile response, and optionally, a second nerve rehabilitation stimulation mode selected to rehabilitate neural transmission in a cavernous nerve, and/or a third penile rehabilitation mode selected to reduce penile fibrosis. Methods of operating the system also are provided.

11 Claims, 17 Drawing Sheets

(52) U.S. Cl.
CPC ..... *A61N 1/36157* (2013.01); *A61N 1/36175* (2013.01); *A61N 1/36192* (2013.01)

(58) Field of Classification Search
USPC .......................................................... 607/39
See application file for complete search history.

(56) References Cited

U.S. PATENT DOCUMENTS

| | | | |
|---|---|---|---|
| 5,215,088 | A | 6/1993 | Normann et al. |
| 5,454,840 | A | 10/1995 | Krakovsky et al. |
| 5,938,584 | A | 8/1999 | Ardito et al. |
| 6,128,536 | A | 10/2000 | Noack et al. |
| 6,169,924 | B1 | 1/2001 | Meloy et al. |
| 6,505,074 | B2 | 1/2003 | Boveja et al. |
| 6,650,943 | B1 | 11/2003 | Whitehurst et al. |
| 6,885,895 | B1 | 4/2005 | Whitehurst et al. |
| 7,006,870 | B1 | 2/2006 | Whitehurst et al. |
| 7,096,070 | B1 | 8/2006 | Jenkins et al. |
| 7,328,068 | B2 | 2/2008 | Spinelli et al. |
| 7,328,069 | B2 | 2/2008 | Gerber |
| 7,330,762 | B2 | 2/2008 | Boveja et al. |
| 7,338,522 | B2 | 3/2008 | Greenberg et al. |
| 7,369,894 | B2 | 5/2008 | Gerber |
| 7,427,280 | B2 | 9/2008 | Gerber |
| 7,734,355 | B2 | 6/2010 | Cohen et al. |
| 7,865,243 | B1 | 1/2011 | Whitehurst et al. |
| 8,630,711 | B1 | 1/2014 | Wark et al. |
| 9,821,163 | B2 | 11/2017 | Fraga Da Silva et al. |
| 10,300,279 | B2 | 5/2019 | Fraga Da Silva et al. |
| 2003/0004553 | A1 | 1/2003 | Grill et al. |
| 2003/0236557 | A1 | 12/2003 | Whitehurst et al. |
| 2004/0049240 | A1 | 3/2004 | Gerber et al. |
| 2004/0073268 | A1 | 4/2004 | Zappala |
| 2005/0010260 | A1 | 1/2005 | Gerber |
| 2005/0131484 | A1 | 6/2005 | Boveja et al. |
| 2005/0283202 | A1 | 12/2005 | Gellman |
| 2006/0129028 | A1 | 6/2006 | Krakousky |
| 2006/0135862 | A1 | 6/2006 | Tootle et al. |
| 2007/0027514 | A1 | 2/2007 | Gerber |
| 2007/0078493 | A1 | 4/2007 | Gerber |
| 2007/0255333 | A1 | 11/2007 | Giftakis et al. |
| 2008/0065167 | A1 | 3/2008 | Boggs, II et al. |
| 2008/0091244 | A1 | 4/2008 | Richardson |
| 2008/0140168 | A1 | 6/2008 | Walter et al. |
| 2010/0016759 | A1* | 1/2010 | Lavoisier ............. A61B 5/4393 600/587 |
| 2013/0123684 | A1 | 5/2013 | Giuffrida et al. |
| 2014/0277266 | A1 | 9/2014 | Khalil et al. |
| 2014/0304773 | A1 | 10/2014 | Woods et al. |
| 2016/0101288 | A1* | 4/2016 | Fraga Da Silva et al. ................. A61N 1/0558 607/39 |

FOREIGN PATENT DOCUMENTS

| | | |
|---|---|---|
| WO | WO-2009023543 A2 | 2/2009 |
| WO | WO-2013011474 A2 | 1/2013 |

OTHER PUBLICATIONS

Burnett, et al., Intraoperative Assessment of an Implantable Electrode Array for Cavernous Nerve Stimulation, J. Sex Med., 5(8):1949-1954 (2008).
Burnett, et al., Neuromodulatory Therapy to Improve Erectile Function Recovery Outcomes After Pelvic Surgery, J. Urol., 176(3):882-887 (2006).
Clavell-Hernandez et al., Penile Rehabilitation Following Prostate Cancer Treatment: Review of Current Literature, Asian J. Andrology, 17:916-922 (Apr. 2015).
Costello, et al., Immunohistochemical Study of the Cavernous Nerves in the Periprostatic Region, BJU Int., 107(8):1210-1215 (2011).
Dean, et al., Physiology of Penile Erection and Pathophysiology of Erectile Dysfunction, Urol. Clin. North Am., 32(4):379-395 (2005).
Eardley, et al., Pharmacotherapy for Erectile Dysfunction, J. Sex. Med., 7:524-540 (2010).
Fode et al., Penile rehabilitation after radical prostatectomy: what the evidence really says, BJU Int., 112(7):998-1008 (2013).
Gandaglia et al., Penile Rehabilitation After Radical Prostatectomy: Does it Work? Transl Androl Urol., 4(2):110-123 (Jan. 2015).
Harding, et al., Comparison of a Needle-Free High-Pressure Injection System with Needle-Tipped Injection of Intracavernosal Alprostadil for Erectile Dysfunction, Int. J. Impot. Res., 14(6):498-501 (2002).
International Search Report and Written Opinion dated Jan. 20, 2016 in Int'l PCT Patent Application Serial No. PCT/IB2015/057809 (0310).
Klotz, et al., Early Experience with Intraoperative Cavernous Nerve Stimulation with Penile Tumescence Monitoring to Improve Nerve Sparing During Radical Prostatectomy, Urology, 52(4):537-542 (1998).
Klotz, et al., Intraoperative Cavernous Nerve Stimulation During Nerve Sparing Radical Prostatectomy: How and When?, Curr. Opin. Urol., 10(3):239-43 (2000).
Leungwattanakij, et al., Intracavernosal Injection and Intraurethral Therapy for Erectile Dysfunction, Urol. Clin. North Am. 28(2):343-54 (2001).
Lue, et al., Electrostimulation and Penile Erection, Urol. Int., 40(1):60-64 (1985).
Lue, et al., Intraoperative Electrostimulation of the Cavernous Nerve: Technique, Results and Limitations, The Journal of Urology, 154:1426-1428 (1995).
Moreland, R.B., Is There a Role of Hypoxemia in Penile Fibrosis: A Viewpoint Presented to the Society for the Study of Impotence, Int'l. J Impotence Research, 10:113-120 (1998).
Mulhall et al., Standard Operating Procedure for the Preservation of Erectile Function Outcomes After Radical Prostatectomy, J Sex Med., 10(1):195-203 (2013).
Muller et al., The Effect of Hyperbaric Oxygen Therapy on Erectile Function Recovery in a Rat Cavernous Nerve Injury Model, J Sex Med., 5(3):562-570 (2008).
Penson et al., 5-Year Urinary and Sexual Outcomes After Radical Prostatectomy: Results From the Prostate Cancer Outcomes Study, J. Urol. 173:1701-1705 (May 2005).
Penson, et al., 5-Year Urinary and Sexual Outcomes after Radical Prostatectomy: Results from the Prostate Cancer Outcomes Study, J. Urol., 179 (5 Suppl): S40-44 (2008).
Ponnusamy, et al., Nerve Mapping for Prostatectomies: Novel Technologies Under Development, J. Endourol., 26(7):769-77 (2012).
Rotella., Phosphodiesterase 5 inhibitors: Current Status and Potential Applications, Nat. Rev. Drug Discov., 1(9):674-682 (2002).
Sadeghi-Nejad., Penile Prosthesis Surgery: a Review of Prosthetic Devices and Associated Complications, J. Sex. Med., 4(4):1520 (2007).
Segal et al., Current Penile-Rehabilitation Strategies: Clinical Evidence, Arab J. Urol., 11:230-0236 (Mar. 2013).
Shafik, A., Extrapelvic Cavernous Nerve Stimulation in Erectile Dysfunction, Human study, Andrologia, 28(3):151-156 (1996).
Shafik, et al., Magnetic Stimulation of the Cavernous Nerve for The Treatment of Erectile Dysfunction in Humans, Int. J. Impot. Res., 12(3):137-141 (2000).
Skoufias et al., Novel Concept Enabling an Old idea: A Flexible Electrode Array to Treat Neurogenic Erectile Dysfunction, J Sex Med., 15:1558-1569 (Sep. 2018).
Takenaka, et al., Variation in Course of Cavernous Nerve with Special Reference to Details of Topographic Relationships Near Prostatic Apex: Histologic Study Using Male Cadavers, Urology, 65(1):136-142 (2005).
Wang, R., Penile Rehabilitation after Radical Prostatectomy: Where Do We Stand and Where Are We Going?, J Sex Med., 4:1085-1097 (2007).

* cited by examiner

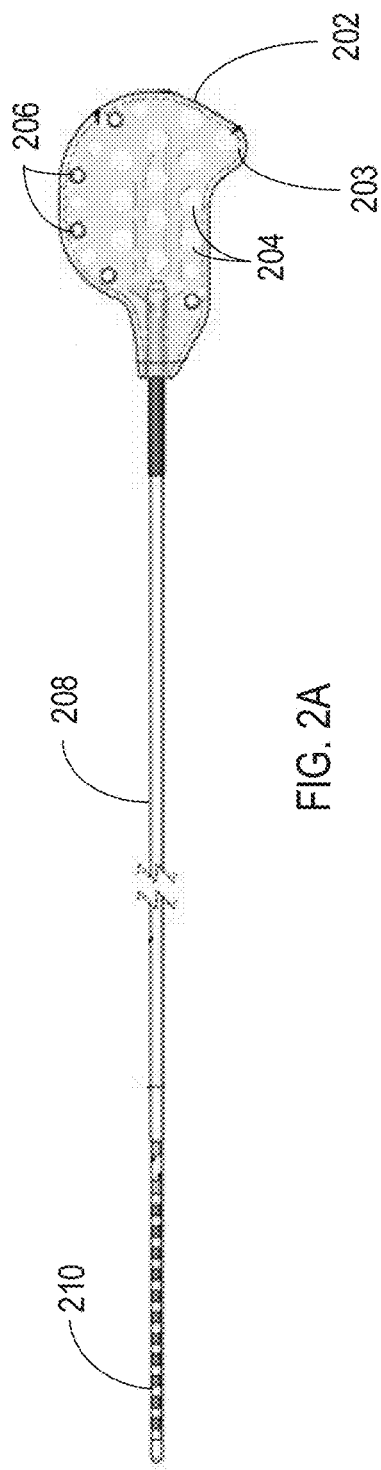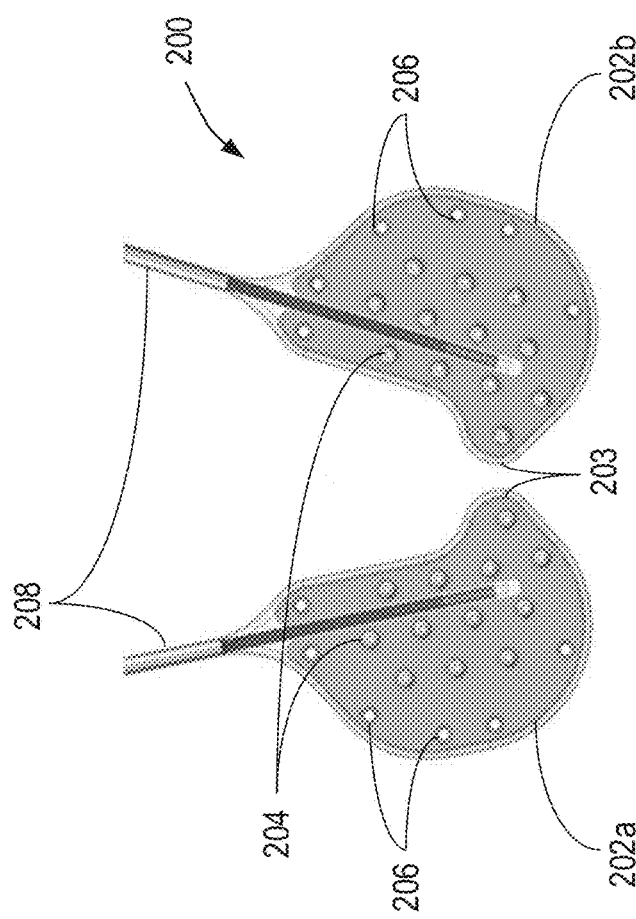
FIG. 2A
FIG. 2B

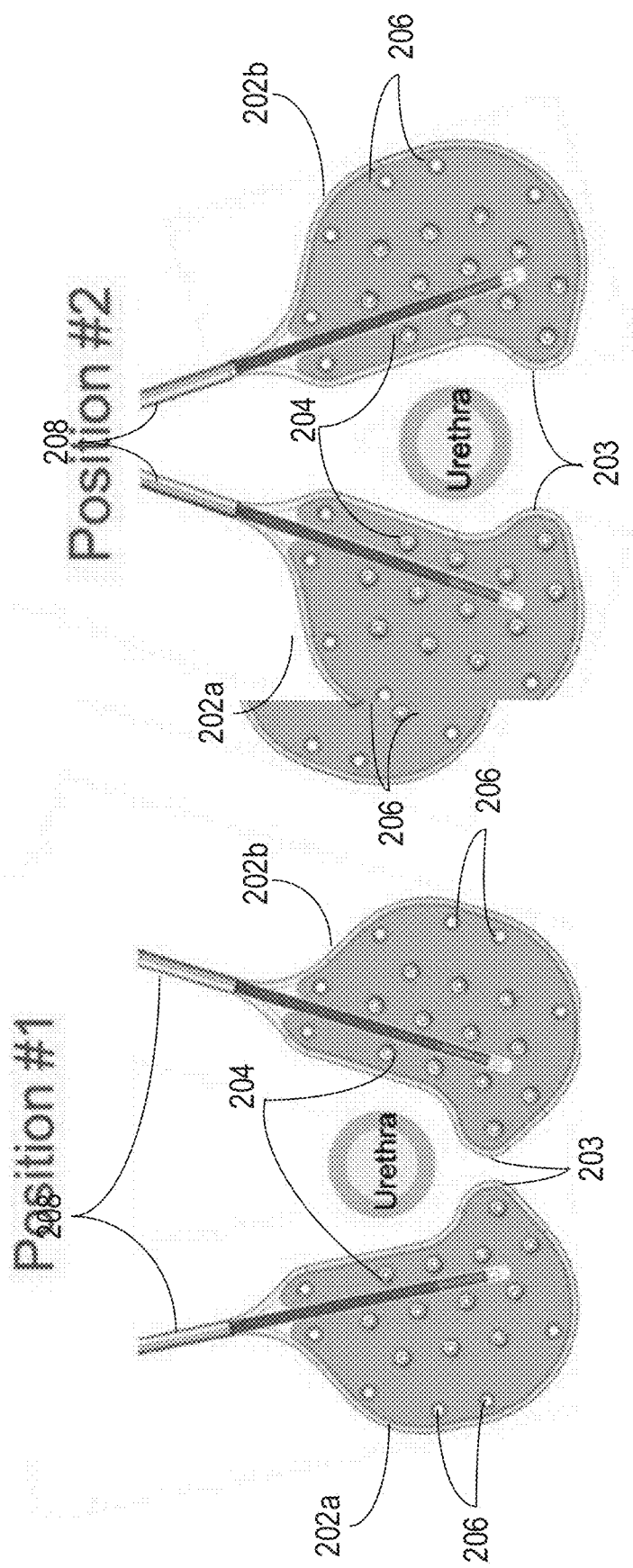

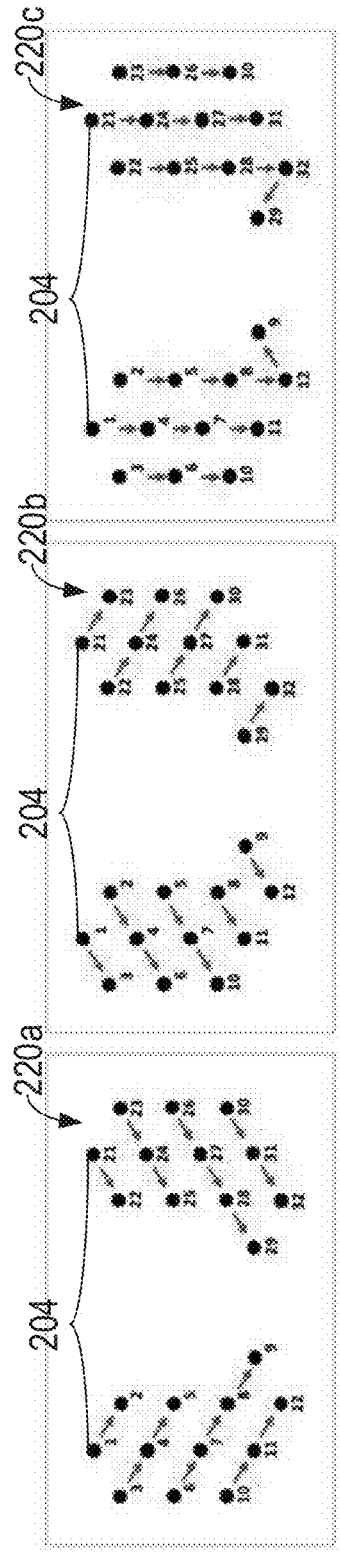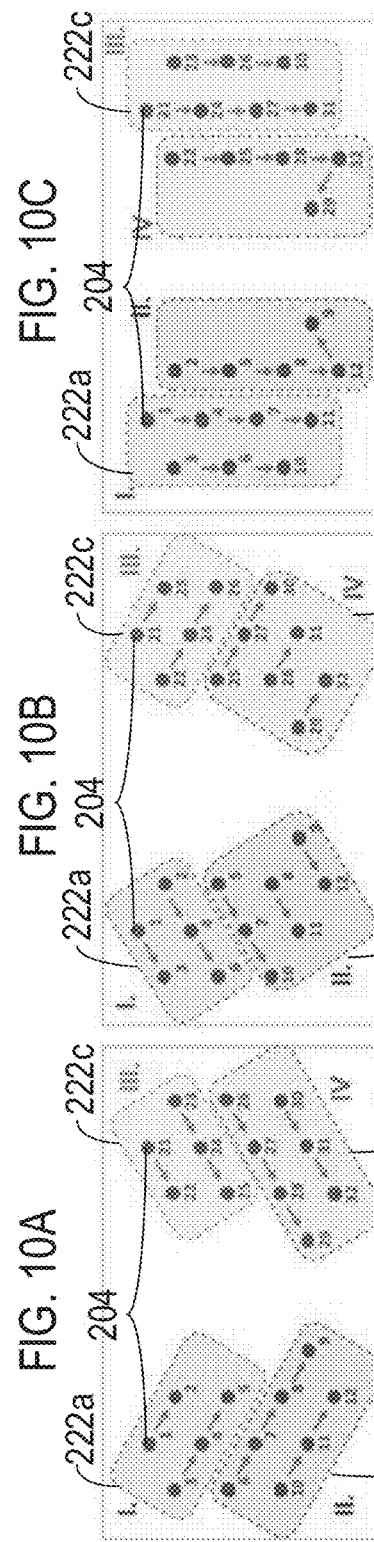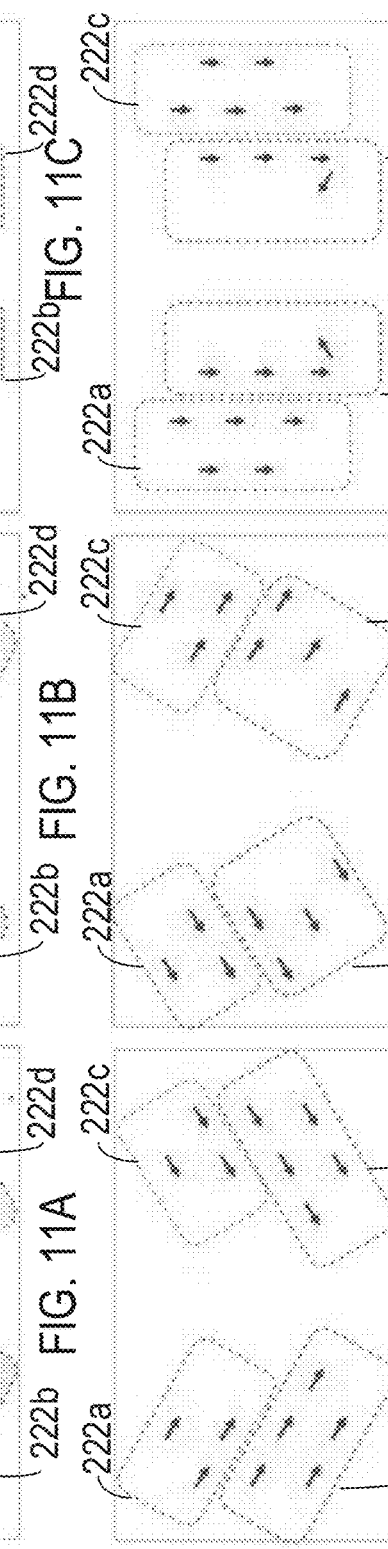

ELECTRO-STIMULATION SYSTEMS AND METHODS FOR REHABILITATION AND TREATMENT OF SEXUAL DISORDERS

FIELD OF THE INVENTION

The present disclosure relates to improved implantable electrical stimulation systems and methods for treating and preventing sexual disorders such as erectile dysfunction, erectile dysfunction following prostatectomy surgery, and erectile dysfunction associated with spinal cord injury. The inventive system also may be used to rehabilitate the cavernous nerves or to reduce penile fibrosis.

BACKGROUND OF THE INVENTION

A sexual disorder (e.g., sexual dysfunction, sexual malfunction) is a complication experienced by an individual, male or female, or a couple during any stage of normal sexual activity, including erection, physical pleasure, desire, preference, arousal, or orgasm. Sexual dysfunctions generally have a profound impact on an individual's quality of life. The most prevalent sexual disorders are erectile dysfunction (ED) and female sexual arousal disorders (FSAD).

Penile erection is a coordinated neurocardiovascular response. See, Dean R C and Lue T F, Physiology of penile erection and pathophysiology of erectile dysfunction, Urol Clin North Am. 2005 November; 32(4):379-95. In the flaccid state, the penile smooth muscles are tonically contracted, allowing only a small amount of blood flow for nutritional purposes. Penile erection occurs when sexual stimulation triggers release of neurotransmitters, mainly nitric oxide, from the cavernous nerve terminals. The neurotransmitters cause relaxation of the smooth muscle cells in cavernosal arterioles and sinuses, resulting in increased blood flow into the penis. This causes the cavernous sinuses to fill with blood and expand against the tunica albuginea, partially occluding the venous outflow, thus resulting in an erection.

ED is a multi-causal disease with diversified etiologies, and may be psychogenic, vasculogenic, hormonal, or neurogenic. However, studies show that the neurogenic and vasculogenic causes are the most prevalent. In general, the major mechanisms responsible for ED are a failure in the neuronal response (e.g., prostatectomy, cystectomy, abdominoperineal resection, spinal cord injury, or diabetes) or an increase in the tone and/or contractility of the smooth muscle within the corpus cavernosum and penile arteries (e.g., hypertension, atherosclerosis and diabetes). See, Sadeghi-Nejad H., *Penile prosthesis surgery: a review of prosthetic devices and associated complications*, Sex Med. 2007 March; 4(2):296-309.

Prostatectomy is known to cause severe ED. This essential surgical procedure, generally for treatment of prostate cancer, often leads to ED due to the inevitable disruption of the neural pathway for erectile function. These intimal nerves are located around the prostate, and may be damaged during the surgery. Currently, surgeons attempt to perform a nerve-sparing surgery; however, in the actual scenario, an astounding 70% of patients undergoing prostatectomy will develop ED. See, Pension D F, McLerran D, Feng Z, Li L, Albertsen P C, Gilliland F D, Hamilton A, Hoffman R M, Stephenson R A, Potosky A L, Stanford J L., *5-year urinary and sexual outcomes after radical prostatectomy: results from the Prostate Cancer Outcomes Study*, J Urol. 2008 May; 179(5 Suppl): S40-4.

Pharmacological treatments are currently available for ED. These drugs (e.g., sildenafil, Viagra®; tadalafil, Cialis® or vardenafil, Levitra®) are efficient for the majority of ED patients; however, they show low effectiveness for ED resulting from prostatectomy or others causes associated with failure in the neuronal response. Such drugs act by potentiating the actions of the neurotransmitter nitric oxide, by inhibiting the enzyme phosphodiesterase type 5 [PDE-5). See, Rotella D P., *Phosphodiesterase 5 inhibitors: current status and potential applications*, Nat Rev Drug Discov. 2002 September; 1(9):674-82. PDE-5 is an enzyme responsible for breaking down the intracellular second messenger cGMP generated by NO stimulus. cGMP is involved in the regulation of some protein-dependent kinases, which relax smooth muscle cells and facilitate erection. Thus, patients with disruption of the erectile neural response do not respond well to such medications. One alternative for these patients is intrapenial injections of vasodilators, which produce direct erection, independent of the neural pathway. See, Leungwattanakij S, Flynn V Jr, Hellstrom W J, *Intracavernosal injection and intraurethral therapy for erectile dysfunction*, Urol Clin North Am. 2001 May; 28(2):343-54 and Harding L M, Adeniyi A, Everson R, Barker S, Ralph D J, Baranowski A P, *Comparison of a needle free high-pressure injection system with needle-tipped injection of intracavernosal alprostadil for erectile dysfunction*, Int J Impot Res. 2002 December; 14(6):498-501. Alprostadil (Prostaglandin E1, PGE1) is the most common vasodilator used for ED. See, Harding and Eardley I, Donatucci C, Corbin J, El-Meliegy A, Hatzimouratidis K, McVary K, Munarriz R, Lee S W, *Pharmacotherapy for erectile dysfunction*, J Sex Med. 2010 January; 7(1 Pt 2):524-40. The vasodilator may be injected into the corpus cavernosum with a needle and is effective in over 80% of patients. See, Harding. Common side effects of intrapenial injection are penile pain, bleeding, hematoma, priapism, and penile fibrosis, which can lead to permanent ED. See, Leungwattanakij.

Another option for these patients is penile implants, which consist of a pair of malleable or inflatable rods surgically implanted within the erection chambers of the penis. See, Sadeghi-Nejad. There are different types of penile prosthesis (rigid, semi-rigid, or inflatable) and all of those prostheses normally require an irreversible and destructive surgery with risk of intra and post-operative complications. Such prosthesis frequently require surgery revision. Nevertheless, prosthesis implantation is a common procedure due to the lack of better treatment options. Thus, there is a clear need for better therapeutic strategy for the treatment of ED resulting from failure of the neural pathway, such as post-prostatectomy ED, providing a painless, safe, easier, non-traumatic and more effective alternative.

Numerous studies have shown that cavernous nerve stimulation can induce and maintain erection in animals and men. See, Lue T F, Schmidt R A, Tanagho E A, Electrostimulation and penile erection, Urol Int. 1985; 40(1):60-4; Shafik A, Shafik A A, Shafik I A, El Sibai 0., *Percutaneous perinea! electrostimulation induces erection: clinical significance in patients with spinal cord injury and erectile dysfunction*, J Spinal Cord Med. 2008; 31(1):40-3; and Shafik A, el-Sibai 0, Shafik A A, *Magnetic stimulation of the cavernous nerve for the treatment of erectile dysfunction in humans*, Int J Impot Res. 2000 June; 12(3):137-41. Since then, electroneurostimulation for erectile response has been considered an option for patients undergoing prostatectomy. The barrier for the development of such technology, however, is the complex anatomy of the human cavernous nerve. See, Klotz L., *Intraoperative cavernous nerve stimulation* during nerve sparing radical prostatectomy: how and when?, Curr Opin Urol. 2000 May; 10(3):239-43 and Ponnusamy K, Sorger J M, Mohr C., *Nerve mapping for prostatectomies: novel technologies under development*, J Endourol. 2012 July; 26(7):769-77. Locating the optimal site for electroneurostimulation is difficult, as the human cavernous nerve travels from the pelvic-plexus to the penis through a complex anastomosis. Moreover, there is significant anatomic variability in the location of the cavernous nerve; the pelvic-plexus is a diaphanous veil with microscopic nerves and the cavernous nerve is not disposed uniformly in every man. Further, each patient's anatomy, disease stage, and cancer location are unique. Collectively, these barriers make the identification of the cavernosal nerve segments for selective stimulation extremely difficult.

In some previously known systems, localization and identification of the cavernosal nerve is conducted during implantation surgery. For example, U.S. Pat. No. 4,585,005 to Lue requires previous identification and isolation of the cavernous nerves. U.S. Pat. No. 7,328,068 to Spinelli describes a method for stimulation of the penile neural pathway that requires precise positioning of the implant to achieve optimal stimulation. In Spinelli, a neurophysiological monitoring assessment could be used as method to locate the optimal stimulation site before implantation. U.S. Pat. No. 7,330,762 to Boveja discloses systems for electroneurostimulation of the cavernosal nerve, including different types of electrodes, such as spiral electrodes, cuff electrodes, steroid eluting electrodes, wrap-around electrodes and hydrogel electrodes. Again, the Boveja system requires identification of the optimal site for stimulation before implantation. U.S. Pat. No. 7,865,243 to Whitehurst describes systems and methods for stimulation of the cavernosal nerve; however, the anatomical identification of the course of the pudendal nerve and/or other nerves to be stimulated must be located before implantation.

Recently, significant gains have been made in achieving practical neuroelectrostimulation systems for treatment of ED that enable localization and identification of the cavernous nerve post implantation. For example, U.S. Pat. Nos. 9,821,163 and 10,300,279 to Fraga da Silva et al., invented by the inventors of the present application, describes neuroelectro stimulation systems wherein electrodes are stimulated post-implantation to empirically determine a preferred electrode excitation configuration to achieve sexual arousal. While the inventions described in those patents represent a significant advance in the use of neuroelectrostimulation to treat ED, it would be desirable to provide methods for reliably determining an electrode excitation configuration for creating arousal in which the electrode excitation configuration can be determined by an automated process.

After bilateral nerve-sparing radical prostatectomy, some patients may recover from erectile dysfunction, especially younger patients without a history or associated-risk factors for ED. However, even if the individual regains erectile function, it typically is over a prolonged period, which may take years. During the recovery period, permanent intrapenial damage may occur, leading to some of permanent ED.

Recent advances in the understanding of post-prostatectomy ED pathophysiology have stimulated debate regarding management of this condition, leading to emergence of the concept of penile rehabilitation after prostatectomy. See, e.g., Wang, R., *Penile rehabilitation after radical prostatectomy: where do we stand and where are we going?*, J Sex Med, 2007, 4(4 Pt 2):1085-97; Segal, R. L. et al., *Current penile-rehabilitation strategies: Clinical evidence*, Arab J Urol, 2013. 11(3): 230-6; Gandaglia, G., et al., *Penile rehabilitation after radical prostatectomy: does it work?*, Transl Androl Urol, 2015, 4(2):110-23; Clavell-Hernandez, J. et al, *Penile rehabilitation following prostate cancer treatment: review of current literature*, Asian J Androl, 2015. 17(6):916-22. The rational for such treatment recognizes that prolonged inability to achieve an erection leads to intracorporeal fibrosis, deteriorating penile structures, and progressive worsening of ED, leading to a permanent state of ED.

As discussed in the foregoing literature references, a regular cycle of penile erection is essential for tissue oxygenation and maintenance of penile function in healthy men. Indeed, physiological nocturnal penile tumescence and spontaneous erection during sleep plays a critical role in the maintenance of organ oxygenation and function. Contrarily, prolonged inability to achieve erection leads to chronic penile hypoxia and consequent fibrogenic cytokine production, as described in Gandaglia; Muller, A., et al., *The effect of hyperbaric oxygen therapy on erectile function recovery in a rat cavernous nerve injury model*, J Sex Med, 2008. 5(3): p. 562-70. This unfavorable local intrapenial environment can result in apoptosis and increased collagen production, altering the cavernosal structures. See, e.g., Gandaglia; Moreland, R. B., *Is there a role of hypoxemia in penile fibrosis: a viewpoint presented to the Society for the Study of Impotence*, Int J Impot Res, 1998. 10(2): p. 113-20.

As further discussed in the above literature references, penile rehabilitation is defined as the use of any medical intervention or combination of interventions, at the time of or after prostatectomy, with a goal of increasing penile blood flow and improving intracorporeal oxygenation to avoid or reduce fibrosis until ability to achieve natural erectile function is recovered. The penile rehabilitation treatment preferably should be applied until nerve regeneration is achieved, which may take from between 12-18 months after prostatectomy up to several years Currently, the state of the art calls for oral PDE5 inhibitors, intracorporeal injection therapy (e.g., Alprostadil), vacuum erection devices, or the combination of these treatments. See, Mulhall, J. P., et al., *Standard operating procedure for the preservation of erectile function outcomes after radical prostatectomy*, J Sex Med, 2013. 10(1):195-203; and Fode, M., et al., *Penile rehabilitation after radical prostatectomy: what the evidence really says*, BJU Int, 2013. 112(7): p. 998-1008. Collectively, clinical trials using these approaches report little or no improvement. See, Clavell-Hernandez; Fode.

In view of the foregoing drawbacks of previously known systems and methods, there exists a need for systems and methods that may be used to methodically identify the location of the cavernous nerves during and/or after implantation and determine the optimal parameters for different modes of activation. There further exists a need for systems and methods that may be used after prostatectomy to increase tissue oxygenation and maintain penile function, thereby reducing fibrosis, and to regenerate the cavernous nerves.

SUMMARY OF THE INVENTION

The present disclosure provides a neuroelectrostimulation system and methods for treating a sexual disorder, including in patients who are incapable of obtaining penile erections spontaneously (e.g., erectile dysfunction (ED) including ED associated with failure in the neuronal response such as post-prostatectomy ED) and patients suffering from female sexual arousal disorder (FSAD), wherein optimization of the electrode excitation configuration and stimulation parameters can be achieved without extensive empirical testing.

An electrical stimulation system for treatment of a sexual disorder, e.g., ED, in a patient may include an implantable stimulation unit, an external patient controller, and an external physician controller, as described in U.S. Pat. Nos. 9,821,163 and 10,300,279, the entireties of which are incorporated herein by reference. The implantable stimulation unit includes an array of electrodes disposed on implantable paddles and a power supply, which may be rechargeable.

In accordance with the principles of the present invention, a programmable controller of the implantable stimulation unit is pre-programmed with routines for optimizing the selection of a subset of the array of excitation electrodes and stimulation parameters to be applied to generate a rapid erectile response, to rehabilitate cavernous nerve transmission post-implantation, and/or to reduce penile fibrosis. The pre-programmed routine also may be activated subsequently, after tissue healing subsequent to the implantation process, to re-optimize selection of the subset of excitation electrodes and/or to adjust the stimulation parameters employed in either the first, rapid response mode, second, nerve rehabilitation mode, or third, penile rehabilitation mode.

In a preferred embodiment, the implantable stimulation unit includes an array of electrodes disposed on a pair of flexible paddles sized and shaped to be implanted at the pelvic plexus for selectively stimulating at least one cavernous nerve. The array of electrodes on each of the pair of paddles is coupled to a programmable controller that includes a stimulation circuit, a nonvolatile memory, and a microprocessor coupled to the stimulation circuit and the nonvolatile memory. In accordance with one aspect of the present invention, the programmable controller is pre-programmed to run an excitation electrode routine that selectively scans the electrode arrays on the paddles with a series of directional current flows, in at least two directions and within at least two regions, to optimize electrode selection for use in stimulating a patient's cavernous nerve.

Upon completion of the electrode selection configuration process, the identity of a preferred subset of the array of electrodes ("excitation electrodes") is defined and stored in non-volatile memory of the programmable controller. Thereafter, the stored electrode configuration is employed with optimized stimulation parameters to stimulate one or more nerves of the pelvic plexus, e.g., at least one cavernous nerve, sufficiently to cause sexual arousal, e.g., an erection. The stimulation regime may consist of stimulation parameters including a pulse duration, frequency, voltage, and current, and may be adjusted post-implantation by an external physician controller and/or an external patient controller.

In a preferred embodiment, the programmable controller initiates the pre-programmed electrode configuration process to cause the stimulation circuit to selectively activate a first series of electrode pairs of the electrode arrays with a first directional current flow to stimulate a cavernous nerve and elicit a first erectile response. Subsequently, the electrode configuration process selectively activates a second series of electrode pairs of the electrode arrays with a second directional current flow to stimulate the cavernous nerve and elicit a second erectile response. The first and second erectile responses then are compared, e.g., by a physician, to select which of the first and second directional current flows provides a more favorable erectile response, thereby determining a preferred current flow direction.

Next, the programmable controller causes the stimulation circuit to selectively activate subsets of the electrode array, using the previously determined preferred current flow direction, to stimulate the cavernous nerve in at least first and second regions. In particular, a first subset of the electrode array in a first region is stimulated to generate a first regional response and a second subset of the electrode array in a second region, different from the first region, is stimulated to generate a second regional response. The first and second regional responses are compared to determine which response is more favorable, and those corresponding regions of electrodes are selected as preferred excitation regions and stored in non-volatile memory for future stimulations.

Then, the programmable controller causes the stimulation circuit to sequentially activate subsets of electrodes within the preferred excitation regions, using the previously determined preferred current flow direction, to elicit a series of erectile response. The series of erectile response are compared to determine which response is more favorable, and those corresponding subsets of electrodes are selected as preferred excitation electrodes and stored in non-volatile memory for future stimulations.

Once preferred excitation regions including preferred excitation electrodes with directional current flows are determined, the programmable controller selectively actives the stimulation circuit to define at least a first stimulation mode in which the applied electrical stimulation invokes a rapid erectile response. In particular, the programmable controller causes the stimulation circuit to serially apply first and second stimulation regimes that employ different stimulation parameters, thereby invoking first and second stimulation responses. The patient physician or patient then may compare the first response to the second response to determine which stimulation regime produces a stronger and/or more rapid erectile response, and selects and stores that stimulation regime as a preferred first stimulation mode in non-volatile memory. In a preferred embodiment, the inventive system may include an external controller that the patient may actuate in an "on demand" mode, e.g., by pushing a button, to activate of the implantable stimulation unit to invoke a rapid erectile response.

In accordance with another aspect of the invention, the programmable controller also may determine a second, nerve rehabilitation stimulation mode, corresponding to a lower current intensity than the first stimulation mode. The nerve rehabilitation stimulation mode is designed to improve transmission of neural activity along at least one cavernous nerve. The programmable controller may be programmed to automatically execute the nerve rehabilitation stimulation pulse sequence at least once per day at one or more specified times, for example, just prior to the patient awakening.

In accordance with another aspect of the invention, the programmable controller also may provide a third, penile rehabilitation stimulation mode, corresponding to a higher current intensity than the second stimulation mode. The penile rehabilitation mode is designed to induce at least partial penile tumescence, to increase tissue oxygenation and reduce the risk of penile fibrosis. The programmable controller may be programmed to automatically execute the penile rehabilitation stimulation pulse sequence at least once per day, and more preferably at one or more specified times, for example, just prior to the patient awakening. Following prostatectomy, both the nerve rehabilitation stimulation mode and penile rehabilitation stimulation mode may be automatically and separately executed at least once per day.

Further in accordance with the principles of the present invention, the programmable controlled may be programmed to reactivate the excitation electrode configuration process and optionally, to select first, second and/or third stimulation modes weeks or months after the implantation procedure is completed. In this manner, selection of the preferred excitation electrodes and/or stimulation regimes may be re-optimized to take into account a healing response of the tissue surrounding the implantable stimulation unit, for example, to address tissue encapsulation. In addition, such re-optimization programming may allow the inventive system to capture improvements in neural transmission achieved by the nerve rehabilitation stimulation mode, such as invoking a rapid erectile response with lower current intensities than initially required post-implantation. Such adjustments may be made under the control of the physician or patient. Alternatively, adjustments to the excitation electrode configuration and/or stimulation regimes of the first, second, and/or third stimulation modes may be made using at least one of machine learning or other form of artificial intelligence.

The external patient controller may be configured to selectively activate the implantable stimulation unit responsive to a patient input to actuate the excitation electrode configuration process, and/or refine the stimulation regimes employed in the first, second, and/or third stimulation modes, to selectively actuate the first stimulation mode on demand, and to set parameters, e.g., activation time(s) and durations for the rehabilitation stimulation modes. The external physician controller is configured to provide similar capability, including selectively activating the excitation electrode configuration process to revise and/or re-optimize the electrode configuration and stimulation regimes stored in the nonvolatile memory. The external physician controller preferably also provides the ability to interrogate the implantable stimulation unit to recover other operational data regarding the status and use of the implantable stimulation unit.

The implantable stimulation unit and the external patient controller preferably communicate wirelessly. Accordingly, the implantable stimulation unit may contain a first transceiver and the external patient controller may contain a second transceiver. The first and second transceivers may employ IEEE 802.11 or BLUETOOTH™ communications schemes. Wireless communications between the first and second transceivers may be encrypted. The external patient controller may be specifically designed for communication with the implantable stimulation unit or may be a smartphone, laptop, tablet, or smartwatch programmed to communicate with the implantable stimulation unit.

The implantable stimulation unit and the external physician controller also preferably communicate wirelessly and the external physician controller may contain a third transceiver. The first and third transceivers may employ IEEE 802.11 or BLUETOOTH™ communications schemes, and wireless communications between the first and third transceivers may be encrypted. The external physician controller may be specifically designed for communication with the implantable stimulation unit or may be a smartphone, laptop, tablet, or desktop computer programmed to communicate with the implantable stimulation unit.

The flexible paddles that carry the electrode arrays preferably sized and shaped to conform to an anatomical shape of a portion of the pelvic plexus, and more preferably, to be implanted laparoscopically. In one embodiment, each of the flexible paddles has a hemispherical shape that conforms to half of the pelvic plexus to provide bilateral stimulation. Each paddle includes an array of at least two rows and two columns of individually addressable electrodes. Each paddle also may include one or more features, such a suture holes or anchors, configured to retain the paddle in contact with the pelvic plexus following radical prostatectomy. The anchors may be, for example, sutures or biocompatible glue. Alternatively or in addition, each flexible paddle may include at least one opening designed to permit connective tissue growth in and/or through the paddle to anchor the paddle adjacent to the pelvic plexus.

Also provided herein are methods for implanting the implantable stimulation unit, methods for programming the implantable stimulation unit to configure preferred excitation electrodes, electrode regions, current directions and stimulation regimes to cause rapid erectile response, rehabilitate neural transmission, or reduce penile fibrosis, and methods for using the system. The implantable stimulation unit and flexible paddles may be sized and shaped for implantation using a robotic-guided surgery system or laparoscopically.

BRIEF DESCRIPTION OF THE DRAWINGS

These and other features, aspects, and advantages of the present disclosure will become apparent from the following description, appended claims, and the accompanying exemplary embodiments shown in the drawings, which are briefly described below.

FIGS. 2A and 2B are, respectively, a plan view of an exemplary flexible paddle suitable for use with the present invention and a plan view of the distal ends of two paddles arranged for positioning against a patient's pelvic plexus.

FIGS. 9A and 9B are, respectively, plan views showing alternative placements of the flexible paddles of the present invention relative to a patient's urethra.

FIGS. 10A-10C depict various directional current flows between adjacent electrode pairs disposed on the flexible paddles of FIG. 2A.

FIGS. 11A-11C depict illustrative regions within the electrode arrays of the flexible paddles of FIG. 2A.

FIGS. 12A-12C depict selection of preferred electrode pairs within various electrode regions in accordance with the present invention.

DETAILED DESCRIPTION OF THE PREFERRED EMBODIMENTS

Systems and methods described herein may be used to treat a sexual disorder such as erectile dysfunction (ED), including ED associated with failure in the neuronal response (resulting from e.g., prostatectomy, cystectomy, abdominoperineal resection, spinal cord injury, and/or diabetes) and ED associated with an increase in the tone and/or contractility of the smooth muscle within the corpus cavernosum and penile arteries (resulting from e.g., hypertension, atherosclerosis, and/or diabetes), and female sexual arousal disorder (FSAD).

Systems and methods described herein are expected to restore function of a denervated penis by, for example, electrostimulating the terminal extremity of the cavernous nerve. The neuronal pathway triggering the erectile response is a parasympathetic input originated from the pelvic splanchnic nerve plexus. The pelvic splanchnic nerve plexus is comprised of branches from the second, third, and fourth sacral nerves that intertwine with the inferior hypogastric plexus, forming the network of nerves in the pelvis. The cavernous nerves are derived from the pelvic splanchnic nerves, travel along via the prostatic plexus, nearly located around the prostate, and supply parasympathetic fibers to the corpora cavernosal and corpus spongiosum of the penis. Therefore, locating the optimal site for electroneurostimulation is difficult, since the human cavernous nerve travels from the pelvic-plexus to the penis through a complex anastomosis. Moreover, there is a significant anatomic variability in the location of the cavernous nerve. Each patient's anatomy, disease stage, and/or cancer location is unique. The pelvic-plexus is a diaphanous veil with microscopic nerves and the cavernous nerves do not follow uniform localization in every man. Therefore, these barriers make identification of the cavernous nerve segments for selective stimulation extremely difficult. Provided herein are systems and methods for overcoming these barriers.

Figure 1:
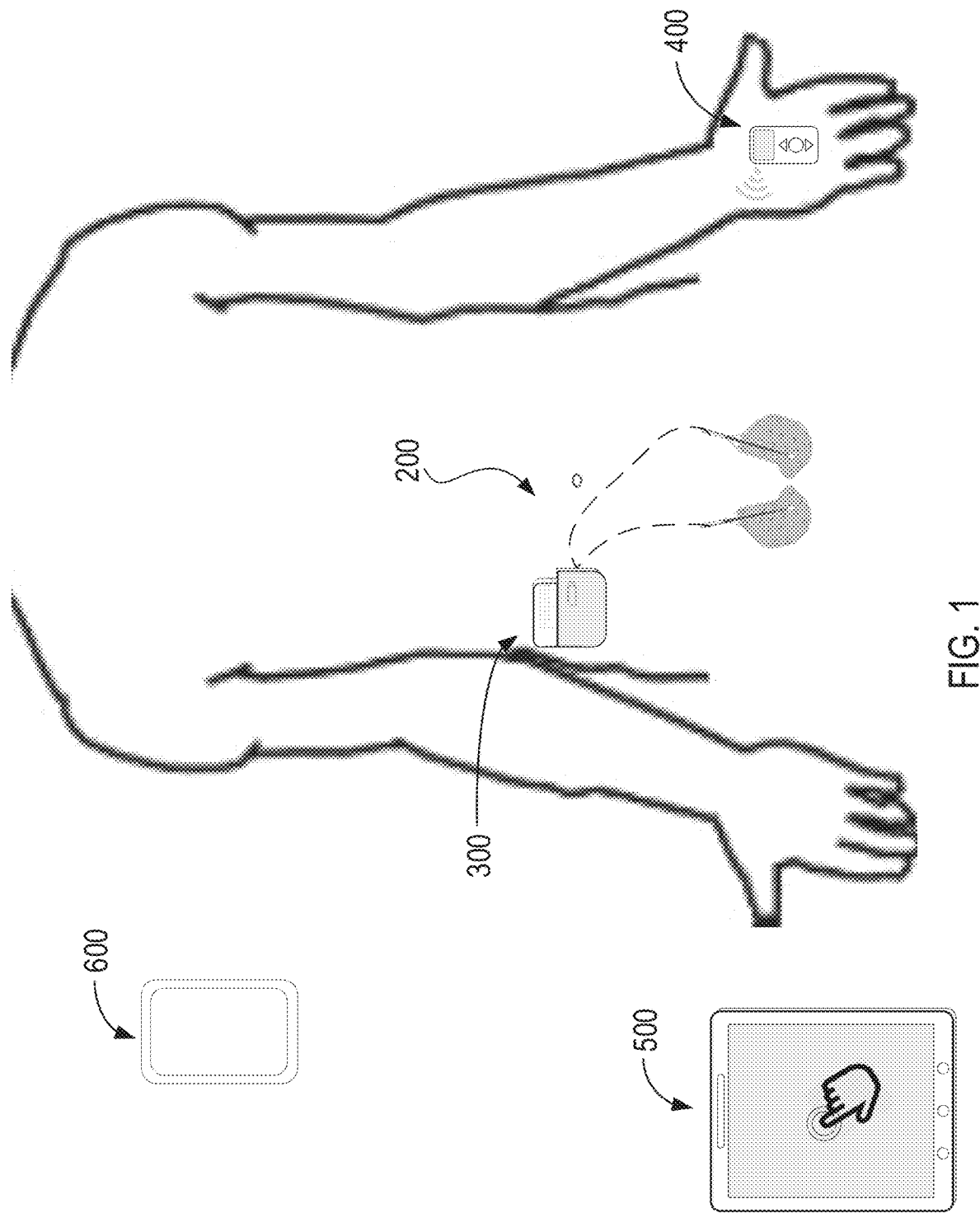
FIG. 1 is a schematic representation of an exemplary electrical stimulation system constructed in accordance with the principles of the present disclosure.

Referring to FIG. 1, an overview of an exemplary electrical stimulation system constructed in accordance with the principles of the present disclosure is provided. In FIG. 1, components of the system are not depicted to scale on either a relative or an absolute basis. Electrical stimulation system 100 may include implantable stimulation unit 200 having programmable controller 300, external patient controller 400, external physician controller 500 and external charger 600.

Referring now also to FIGS. 2A and 2B, implantable stimulation unit 200 includes at least one flexible paddle, illustratively first flexible paddle 202a and second flexible paddle 202b, each comprising an array of electrodes 204 and suture holes 206, cable 208, and programmable controller 300. Each electrode 204 may be individually selected to emit electrical energy to stimulate tissue. Preferably, electrodes 204 are selected in one or more pairs by a programmable controller of implantable stimulation unit 200 to cause stimulation of erectile tissue when activated by a user or physician, e.g., using external patient controller 400 or physician controller 500. Electrodes 204 may be arranged uniformly and/or disposed in different spatial configuration. For example, electrodes 204 may be spaced apart by about 0.05 mm to about 5.0 mm, and more preferably about 0.5 mm to about 1.5 mm. Illustratively, electrodes 204 are arranged in a plurality of rows and a plurality of columns, and the number of electrodes 204 may vary according to need between about 10 to over 50 electrodes. Electrodes 204 may apply bipolar stimulation, such that current passes from one electrode to another electrode to stimulate a nerve or a group of nerves disposed there between. The arrays of electrodes 204 may have a tissue-friendly shape designed to reduce adverse tissue reaction that may lead to formation of fibrotic encapsulation. For example, electrodes 204 may be sized and shaped such that a convex, spherical, or flat shaped portion is exposed on the flexible substrate, avoiding sharp surfaces that may damage or irritate the tissue. Electrodes 204 may be made of platinum, gold, or other conductible implantable material suitable for electrical stimulation of nerves.

Flexible paddles 202 preferably are sized and shaped to abut at least a portion of a pelvic plexus of a patient. As shown in FIGS. 2A and 2B, first flexible substrate 202a is configured to conform to a first half of the pelvic plexus and second flexible paddle 202b is configured to conform to a second half of the pelvic plexus. The flexible paddles may bend to form an arc shape that conforms to the pelvic plexus, and may be implanted thereon, e.g., during prostatectomy surgery. Preferably, flexible paddles 202 conform to an anatomical shape of a portion of the pelvic plexus and may cover part or the entire area of the pelvic plexus so that electrodes 204 are in optimal contact with a cavernous nerve. The flexible paddles may comprise a structural matrix of silicone or other flexible electrically non-conductive material, which allows adaptation and molding to the local anatomy optimize placement and to minimize tissue reaction. The flexible paddles may have a flat structure designed in a suitable shape (e.g., hemisphere, rectangular, squared, oval, ellipse or trapezoid) and dimensioned to better adapt to each patient's anatomy and need.

Referring again to FIG. 1, implantable stimulation unit 200 includes a first array of electrodes 204 disposed on first flexible paddle 202a and a second array of electrodes 204 disposed on second flexible paddle 202b. Programmable controller 300 preferably is programmed to activate the stimulation circuit to cause one or more electrodes 204 disposed on first flexible paddle 202a and one or more electrodes 204 disposed on second flexible paddle 202b to simultaneously apply bilateral electrical stimulation to a patient's erectile.

Implantable stimulation unit 200 may include at least one anchor, preferably individually coupled to the flexible paddles, to maintain the flexible paddles in contact with the pelvic plexus. The anchor may consist of sutures, a biocompatible matrix, a biocompatible glue or some combination thereof. In one preferred embodiment, each flexible paddle includes one or more suture holes 206 through which a suture may anchor the flexible paddle to the pelvic plexus. Implantable stimulation unit 200 may be encapsulated in one or more biocompatible materials suitable for long-term implantation (e.g., titanium cage, silicone cage). In one embodiment, flexible paddles 202 may include one or more cavities disposed between electrodes 204 or within specific regions of the paddles to permit connective tissue growth in and/or through the paddle to enhance anchoring and fixation in the pelvic cavity.

Cable 208 electrically couples electrodes 204 of flexible paddles 202a and 202b to programmable controller 300. Cable 208 may be an insulated multi-conductor cable having an independent wire for each electrode 204. Cable 208 may include branches, as illustrated, permitting connection with the flexible paddles. In one embodiment, more than one cable 208 may be coupled to each of array of electrodes 204 of first flexible paddle 202a and second flexible paddle 202b.

Programmable controller 300 may be implanted in the lower lateral abdomen between the umbilic and iliac crest lines and includes circuitry configured to store stimulation routines and to cause the stimulation circuit to supply electrical stimulation at parameters defined by the stimulation regimes to selected subsets of electrodes 204. Parameters employed in such stimulation regimes may include pulse duration, frequency of alternating current, voltage, current and period of stimulation.

Programmable controller 300 may be controlled by, and optionally powered by, external patient controller 400. External patient controller 400 preferably includes user interface 402 that permits a user, e.g., patient, physician, caregiver, to adjust a limited number of operational parameters of programmable controller 300 including starting and stopping a stimulation session. Programmable controller 300 communicates with external patient controller 400 via respective communication units, which may each include an inductive coil and/or RF transceiver to communicate information in a bidirectional manner across a patient's skin and, optionally, to transmit power to programmable controller 300. For example, external patient controller 400 may selectively activate programmable controller 300 responsive to user input received at user interface 402 via respective telemetry (or RF) systems in programmable controller 300 and external patient controller 400.

In a preferred embodiment, a limited number of stimulation parameters may be adjusted at user interface 402 to lessen the chance of injury caused by maladjustments made by non-physician users. In an alternative embodiment, external patient controller 400 also may send adjustments to stimulation parameters, e.g., electrodes used to apply stimulation, pulse duration, frequency of alternating current, voltage, current, and period of stimulation, to programmable controller 300, responsive to user input received at user interface 402. In one embodiment, external patient controller 400 may activate pre-programmed routines stored in programmable controller 300 to identify an optimized set of excitation electrodes and to store the identity of those electrodes in non-volatile memory, as described herein below.

External patient controller 400 may be specifically designed for use with implantable stimulation unit 200 and programmable controller 300. Alternatively, external patient controller 400 may be a smartphone, laptop, tablet, smartwatch, or the like programmed to communicate with implantable stimulation unit 200 via an application or "app" downloaded from an app store. In either case, external patient controller 400 is programmed to interface with implantable stimulation unit 200 and/or external physician controller 500, and may use cellular, 802.11 WiFi, Zigbee, and/or BLUETOOTH™ chipset(s) for communication with those devices. Specifically, external patient controller may be programmed to selectively activate programmable controller 300 responsive to patient input.

External physician controller 500 is programmed to communicate with programmable controller 300 either directly or via external patient controller 400. As shown in FIG. 1, external physician controller 500 illustratively may be a computer having a non-transitory computer readable medium programmed with instructions that, when run on the computer, cause the computer to provide programming to programmable controller 300. External physician controller 500 may be coupled wirelessly to programmable controller 300 and/or external patient controller 400 such that external physician controller 500 may download for review data stored on programmable controller 300 and/or external patient controller 400. External physician controller 500 also may transfer programming data to programmable controller 300 to reprogram stimulation parameters programmed into programmable controller 300. For example, external physician controller 500 may be used to program and adjust parameters such as pair(s) of electrodes to be used for stimulation, pulse duration, frequency of alternating current, voltage, current, and period of stimulation. External physician controller 500 also may be programmed to upload and store data retrieved from programmable controller 300 to a remote server for later access by a physician. In one embodiment, external physician controller 500 may selectively activate desired subsets of electrodes 204 and to cause nonvolatile memory of programmable controller 300 to store the identity of those electrodes and a stimulation routine sufficient to cause sexual arousal or nerve or penile rehabilitation, as described further below.

External physician controller 500 may selectively activate programmable controller 300 to execute a scanning protocol stored in nonvolatile memory which, when activated, determines preferred pairs of electrodes, current flow directions, and electrode regions that cause a rapid erectile response, enable neural rehabilitation, and/or reduce penile fibrosis, and to store the identity of those electrodes in the nonvolatile memory of programmable controller 300. More specifically, the scanning protocol may cause a microprocessor of programmable controller 300 to supply electrical stimulation via the stimulation circuit by selectively activating electrodes 204 of the array in a predetermined manner to determine preferred directions of current flow, preferred regions of electrodes when stimulated in the preferred direction of current flow, preferred pairs of electrodes within the preferred region of electrodes, and preferred stimulation parameters to be applied to those preferred electrodes, as described herein below. The scanning protocol may be used to determine a stimulation pulse sequence corresponding to an erection mode of activation, and optionally, a nerve rehabilitation stimulation pulse sequence corresponding to a rehabilitation mode of activation for rehabilitation of at least one cavernous nerve, and/or a penile rehabilitation stimulation pulse sequence corresponding to a rehabilitation mode of activation for inducing at least partial penile tumescence and reducing penile fibrosis.

In one embodiment, external physician controller 500 may be used in a post-operative (e.g., prostatectomy) period to determine preferred electrode pairs and preferred stimulation parameters that yield a favorable rapid erectile response or for nerve or penile rehabilitation. External physician controller 500 may be used to cause the nonvolatile memory of programmable controller 300 to store a first stimulation regime that invokes a rapid erectile response when activated on demand by external patient controller 400 and a second stimulation regime, activated via external patient controller 400 or automatically by programmable controller 300 at pre-set times to provide a lower current intensity to rehabilitate neural transmission via at least one cavernous nerve. The stimulation regimes are stored within memory of programmable controller 300 such that erection may be achieved using those parameters at a later time, e.g., responsive to user input at external patient controller 400.

External physician controller 500 may be specifically designed for use with implantable stimulation unit 200. Alternatively, external physician controller 500 may be a smartphone, laptop, tablet, desktop computer, or the like programmed to communicate with implantable stimulation unit 200. Accordingly, external physician controller 500 may use software such as an application or "app" downloaded from an app store to interface with implantable stimulation unit 200 and/or external patient controller 400, and may use cellular, 802.11 WiFi, Zigbee, and/or BLUETOOTH™ chipset(s) for communication with those devices. External physician controller 500 may communicate directly with implantable stimulation unit 200 or with implantable stimulation unit 200 via external patient controller 400.

External charger 600 may electrically communicate with programmable controller 300 and transcutaneously charge programmable controller 300 via respective inductive coils. External charger 600 may generate an alert via an indicator LED, audible alarm, or vibration motor when a power level of programmable controller 300 is below a threshold power level.

Figure 3:
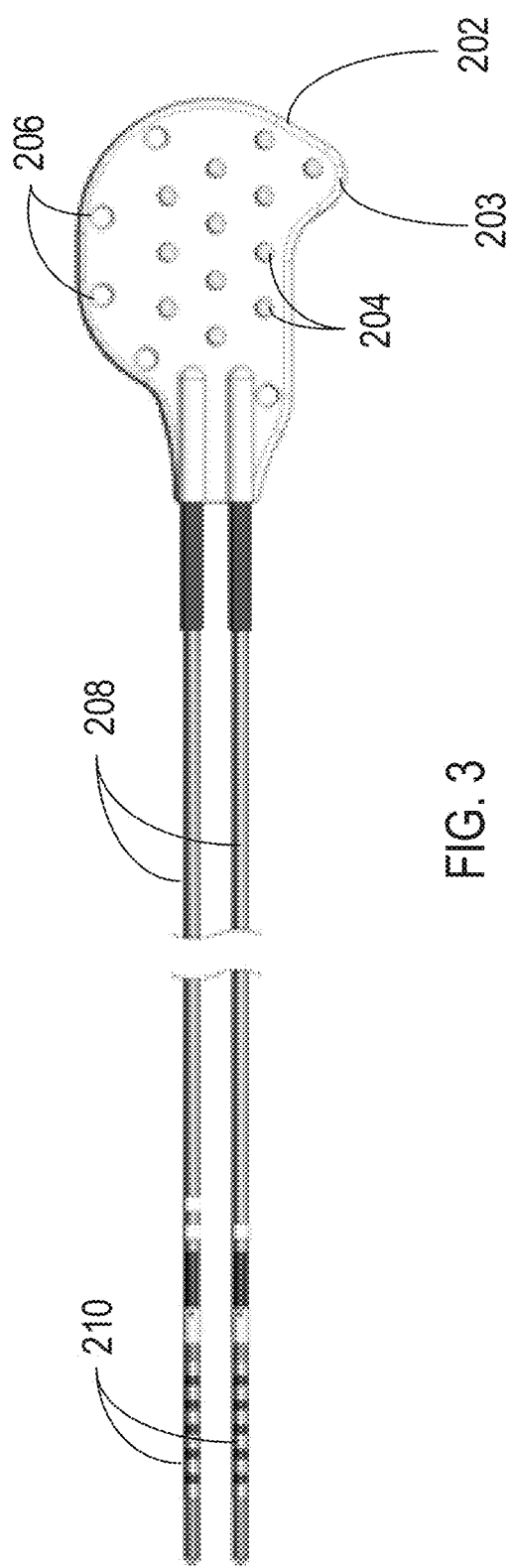
FIG. 3 is a plan view of an alternative embodiment of a flexible paddle suitable for use with the system of the present invention.

Referring now to FIGS. 2A, 2B and 3, exemplary paddle designs of an implantable stimulation unit are illustrated. Implantable stimulation unit 200 may include at least one flexible paddle 202 having an array of electrodes 204 and suture holes 206. Flexible paddles 202 may be operatively coupled to programmable controller 300 via cable 208 having leads 210. Cable 208 may be an insulated multi-conductor cable having an independent wire for each electrode 204. FIG. 2A depicts an embodiment in which single cable 208 couples flexible paddle 202 to programmable controller 300. Alternatively, as shown in FIG. 3, two or more cables 208 may be provided to couple flexible paddle 202 to programmable controller 300. In the embodiment of FIG. 3, one of the cables of cables 208 may electrically couple a first subset of the array of electrodes 204, e.g., six electrodes, to programmable controller 300, and the other cable 208 may electrically couple a second subset of the array of electrodes 204, e.g., the remaining six electrodes, to programmable controller 300. Thus, programmable controller 300 may include multiple ports for receiving cables 208.

Flexible paddle 202 may bend, e.g., to assume an arc shape, and may be implanted (e.g., during prostatectomy surgery) in contact with the pelvic plexus. Preferably, flexible paddle 202 may be conformed to an anatomical shape of a portion of the pelvic plexus. Flexible paddle 202 may comprise at least two rows and at least two columns of electrodes 204. In a preferred embodiment depicted in FIG. 2B, the array of electrodes 204 may include 12 electrodes on each of first flexible paddle 202a and second flexible paddle 202b. Flexible paddle 202 may have a substantially hemispherical shape, including protruding portion 203 that extends from a corner of the flexible paddle farthest from cable 208. The hemispherical shape is selected to avoid damaging soft tissue, minimize injury, and reduce fibrotic encapsulation, which may impede transfer of stimulation pulses from the electrodes to the nerves. Protruding portion 203 also allows the flexible paddle to be placed adjacent to the cavernous nerves while accommodating the anatomy of the region, as described below with respect to FIGS. 8A and 8B. At least one electrode 204 may be disposed on protruding portion 203 of the paddle.

Still referring to FIG. 2B, a two-paddle embodiment is described. In this embodiment, the stimulation unit 200 (see FIG. 1) includes first flexible paddle 202a and second flexible paddle 202b, each having an array of electrodes 204 and suture holes 206. Each of first flexible paddle 202a and second flexible paddle 202b is coupled to programmable controller 300 via cables 208. Alternatively, a single cable 208 may include branches that couple paddles 202a and 202b to programmable controller 300. Because the pelvic plexus generally has two nerve groups, first flexible paddle 202a and second flexible paddle 202b may each cover part or the entire area of one nerve group so that at least one of the arrays of electrodes 204 is in contact with a cavernous nerve. For example, first flexible paddle 202a and second flexible paddle 202b may be implanted within a patient such that protruding portions 203 of each hemispherical paddle face each other, as shown in FIG. 2B. Protruding portions 203 thus may permit the flexible paddles to be placed surrounding the urethra, as shown in FIGS. 9A and 9B, as described below. In a preferred embodiment, each flexible paddle 202 has a thickness of about 2 mm, a length of about 32.5 mm, and a width of about 18 mm, except that protruding portion 203 extends to a width of about 22 mm. First flexible paddle 202a and second flexible paddle 202b may have the same or different dimensions. The distance between the two paddles, when implanted, may be between about 0.5 mm and about 8 cm.

Figure 4A:
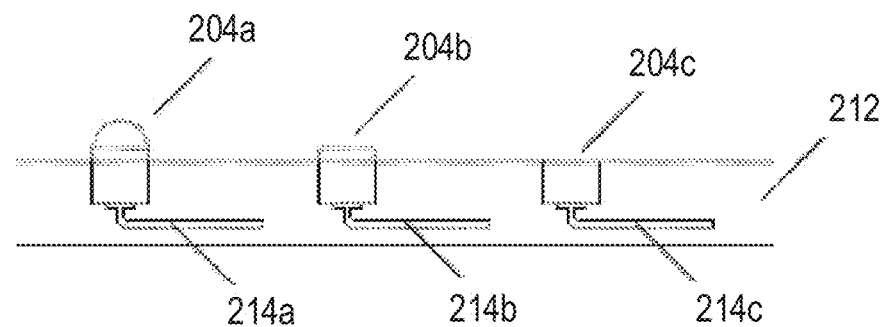
FIGS. 4A and 4B are, respectively, side sectional and perspective line drawing views of different electrode shapes for use in the flexible paddles of FIGS. 2 and 3, while FIGS. 4C to 4E depicted charge distribution over the various electrode shapes depicted in FIGS. 4A and 4B.
Figure 4B:
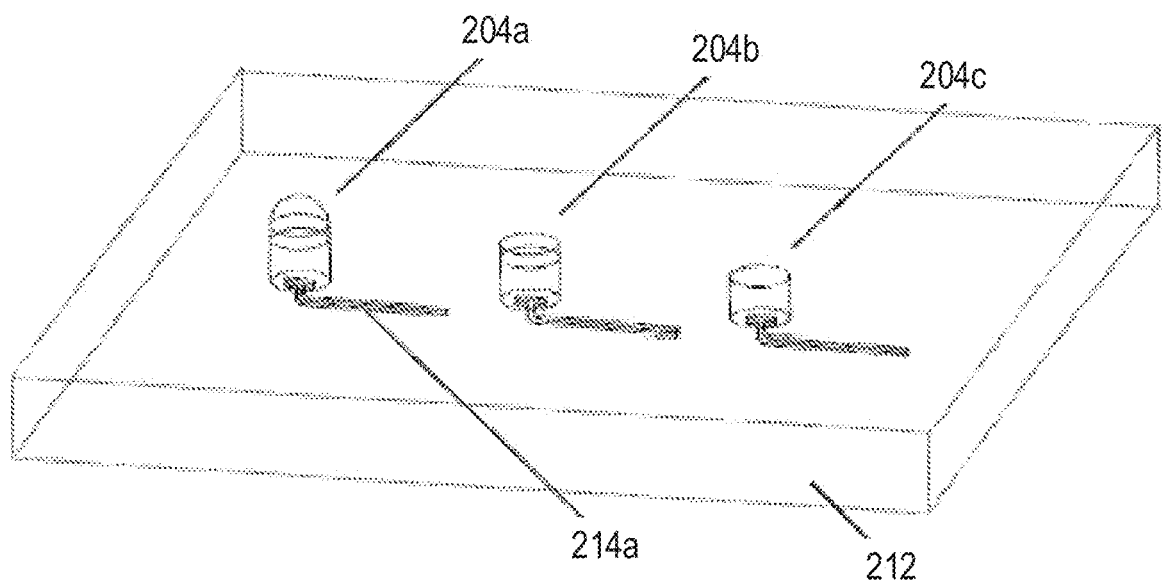

Referring now to FIGS. 4A and 4B, exemplary electrode shapes for use in implantable stimulation unit 200 are described. Electrodes 204a, 204b and 204c each have a tissue friendly shape configured to reduce adverse tissue reaction that may lead to fibrosis formation around the electrode. Electrode 204a has a spherical portion extending from flexible substrate portion 212 and is independently coupled to the circuitry of programmable controller 300 by wire 214a of the cable. Electrode 204b has a flat portion extending above the height of flexible substrate portion 212 and is independently coupled to the circuitry of programmable controller 300 by wire 214b of the cable. Electrode 204c is flat and is flush with the surface of flexible substrate portion 212 and is independently coupled to the circuitry of programmable controller 300 by wire 214c of the cable. Advantageously, each of the electrode shapes does not have a sharp surface that may damage or irritate the tissue. As will also be understood by one of skill in the art, the array of electrodes 204 may use one, two, or three of these electrodes shapes or other suitable tissue friendly shapes.

Figure 4C:
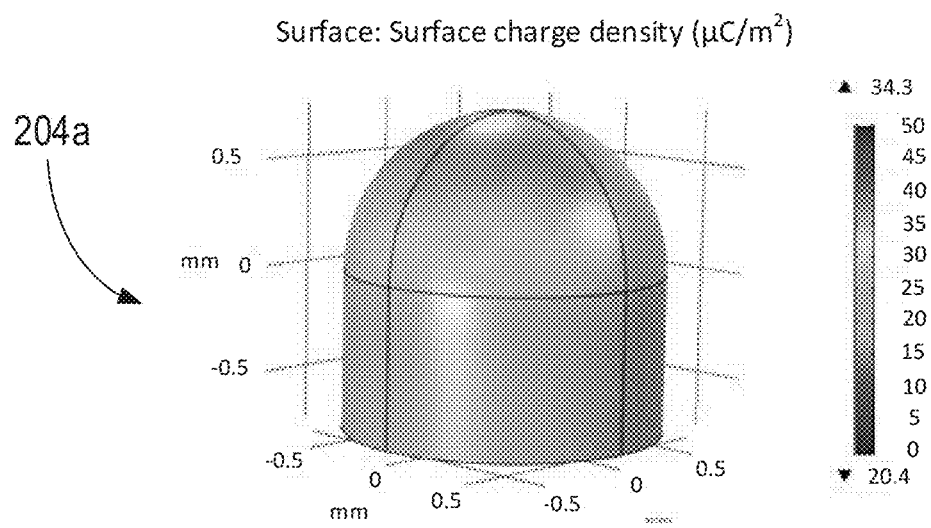
Figure 4D:
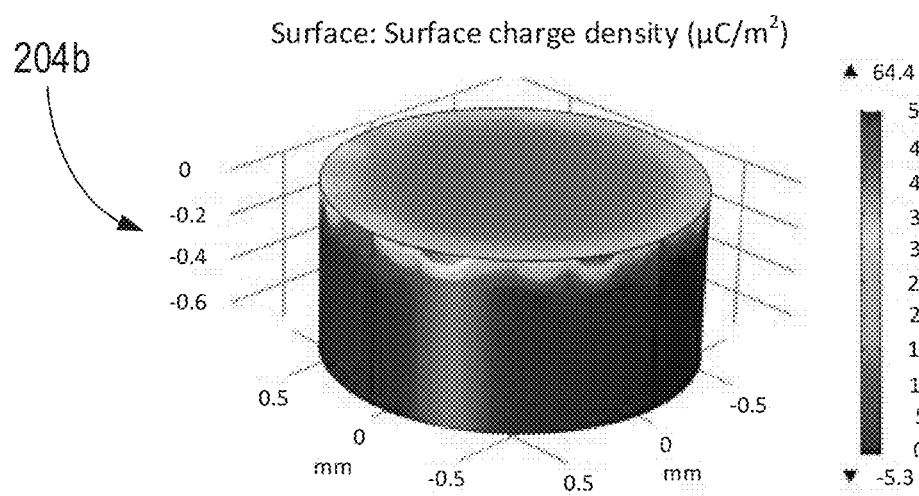
Figure 4E:
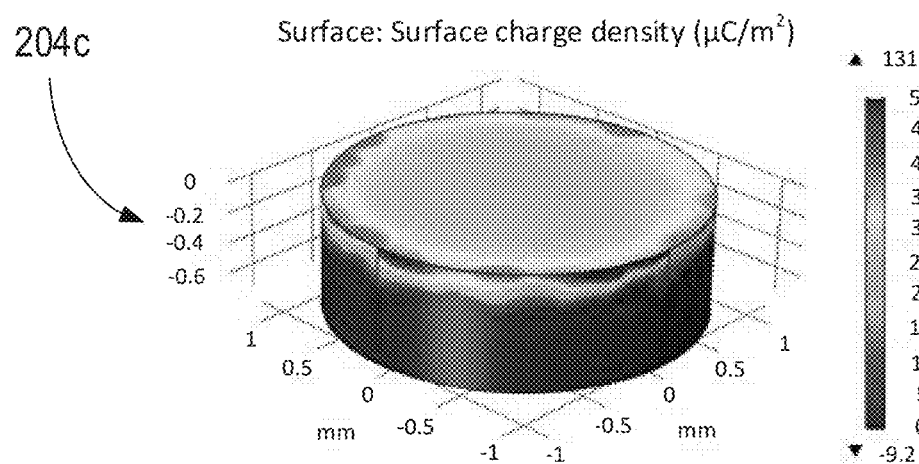

Referring now to FIGS. 4C to 4E, exemplary electrode shapes are further described, in which FIGS. 4C to 4E depict the surface charge density for each electrode shape. As shown in FIG. 4C, the hemispherical shape of electrode 204a allows a homogenous charge distribution over the surface of the electrode, thereby providing efficient transfer of energy from the electrode to the cavernous nerves, without damage to the surrounding tissues. In contrast, as the charge distributions of flat disc electrodes 204b and 204c, as depicted in FIGS. 4D and 4E, exhibit large accumulation of charges on the perimeter of the electrodes, which may impede energy transfer and possibly contribute to tissue damage.

Figure 5:
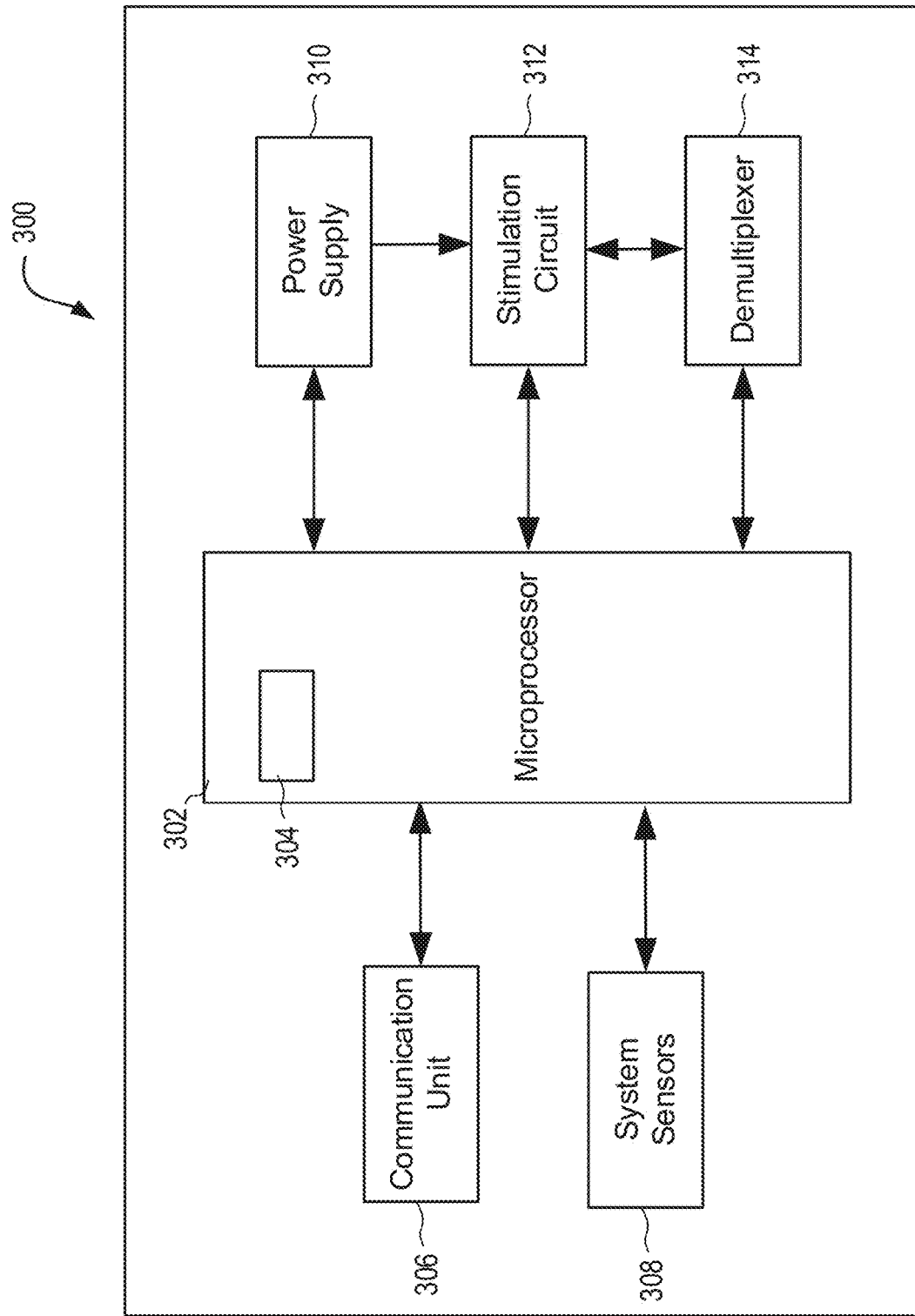
FIG. 5 depicts a generalized block diagram of an exemplary programmable controller of an implantable stimulation unit of the stimulation system of FIG. 1.

With respect to FIG. 5, a generalized schematic diagram of the internal functional components of programmable controller 300 is now described. Programmable controller 300 is programmed to cause stimulation of preferred excitation electrodes in accordance with stimulation regimes stored in the memory of programmable controller 300. Programmable controller 300 preferably includes microprocessor 302, nonvolatile memory 304, communication unit 306, system sensors 308, power supply 310, stimulation circuit 312, and demultiplexer 314.

Microprocessor 302 is electrically coupled to and controls the functional components of programmable controller 300. Microprocessor 302 may comprise a commercially available microcontroller unit including a programmable microprocessor, volatile memory, nonvolatile memory 304 such as EEPROM for storing programming and nonvolatile storage, e.g., Flash memory, for storing firmware and a log of system operational parameters and patient data. The memory of microprocessor 302 stores program instructions that, when executed by microprocessor 302, cause the processor and the functional components of programmable controller 300 to provide the functionality ascribed to them herein. Microprocessor 302 preferably is programmable such that programming data (e.g., stimulation regimes, identity of excitation electrodes, stimulation parameters, etc.) is stored in nonvolatile memory 304 of microprocessor 302 and may be adjusted using external patient controller 400 and/or external physician controller 500.

Microprocessor 302 may be programmable to allow electrical stimulation of any chosen combination of electrodes 204 on the array, thus providing a simple bipolar configuration. Microprocessor 302 further may be programmed with a routine to selectively activate desired subsets of the array of electrodes 204 to determine a subset of the array of electrodes and one or more stimulation regimes that provide beneficial stimulation, and store that information in nonvolatile memory 304 for subsequent use by microprocessor 302. As used in this disclosure, the term "excitation electrodes" refers to a subset of electrodes determined to provide a preferred erectile response for a preferred current flow direction. Further as used in this disclosure, the term "stimulation regime" refers to the set of stimulation parameters that, when applied to the excitation electrodes, is adjudged by the patient or physician to invoke a favorable rapid erectile response or provide stimulation determined by the patient or physician as favorable to restoring or strengthening neural transmission via at least one cavernous nerve.

For example, microprocessor 302 may direct power supply 310 to send an electrical signal via stimulation circuit 312 to the set of excitation electrodes 204, using demultiplexer 314, which emit electrical power. The stimulation regime used by microprocessor 302 to supplies electrical stimulation via stimulation circuit 312 and the pelvic plexus to at least one cavernous nerve sufficient to cause sexual arousal, e.g., an erection, or for nerve or penile rehabilitation. The routine may activate the identified and stored subsets of electrodes automatically and/or responsive to user input at external patient controller 400 and/or external physician controller 500. In addition, as described below, non-volatile memory 304 stores pre-programmed routines for scanning the arrays of electrodes to enable identification of the set of excitation electrodes and stimulation parameters for the preferred stimulation regimes both initially after implantation of implantable stimulation unit 200 and at later times post implantation, as may be directed the external patient controller 400 or external physician controller 500. The set of excitation electrodes yields the best sexual arousal, e.g., erectile response, and is stored in memory. The identity of the set of excitation electrodes is stored for later stimulation and also may be transmitted to external patient controller 400 and/or external physician controller 500.

The stimulation parameters are selected to provide sexual arousal, to promote nerve regeneration, and/or to improve nerve regeneration to treat sexual disorders such as erectile dysfunction and female sexual arousal disorder. For example, stimulation may cause and maintain an erection and may promote and/or improve nerve (e.g., nerve(s) of the pelvic plexus and/or cavernous nerve(s)) regeneration over time. As an example, pulse duration may be programmed to be between about 0.5 msec to about 10 msec, about 0.5 msec to about 5 msec, about 1 msec to about 4 sec, or about 1 msec to about 3 msec. Frequency of alternating current may be programmed to be between about 10 Hz to about 30 Hz, about 10 Hz to about 25 Hz, about 10 Hz to about 20 Hz, or about 15 Hz to about 25 Hz. Voltage may be programmed to be between about 1 V to about 15 V, about 5 V to about 10 V, about 1 V to about 5 V, or about 10 V to about 15V. Current may be programmed to be between about 1 milliamp to about 100 milliamps, about 1 milliamp to about 50 milliamps, about 1 milliamp to about 20 milliamps, about 20 milliamps to about 50 milliamps, about 50 milliamps to about 100 milliamps, or about 75 milliamps to about 100 milliamps. Period of stimulation may be programmed to automatically stimulate during predetermined times or may stimulate responsive to user input, e.g., at user interface 402. For example, stimulation may be maintained during a portion or during the entire period of desired erection. For nerve regeneration, it may be preferable to stimulate at predetermined intervals over time. For example, automatic stimulation may occur hourly, once a day, twice a day, three times a day, four times a day, every other day, every three days, or weekly for a period of 10 min to 2 hours, 10 min to 1 hour, 10 min to 30 min, 10 min to 20 min, or 1 hour to 2 hours. Preferably, stimulation for nerve regeneration occurs using oscillating current or low-frequency electrical stimulation.

Microprocessor 302 is coupled to communication unit 306 having circuitry configured to communicate external patient controller 400 and/or external physician controller 500. Communication unit 306 permits transmission of stimulation commands, and optionally power, between programmable controller 300 and external patient controller 400 such that programmable controller 300 may be powered, programmed, and/or controlled by external patient controller 400. For example, microprocessor 302 may start or stop a stimulation session or to conduct an assessment to determine a preferred subset of the array of electrodes 204 responsive to stimulation commands received from a corresponding communication unit (e.g., an inductive unit having a telemetry system and coil and/or a RF unit having a transceiver and antenna) of external patient controller 400. Communication unit 306 further permits transmission of programming data, and optionally power, between programmable controller 300 and external physician controller 500 such that programmable controller 300 may be powered, programmed, and/or controlled by external physician controller 500. For example, microprocessor 302 may direct changes to electrodes included in the set of excitation electrodes used for stimulation, as well as the preferred stimulation regimes, including pulse duration, frequency of alternating current, voltage, current, and/or period of stimulation responsive to programming data received from a corresponding communication unit (e.g., an inductive unit having a telemetry system and coil and/or a RF unit having a transceiver and antenna) of external physician controller 500.

Communication unit 306 may include a telemetry system electrically coupled to an inductive coil. The technology for telemetry systems and coils is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, the coil may be used to transmit power only, and separate radio frequency transmitters may be provided in programmable controller 300, external patient controller 400, and/or external physician controller 500 for establishing bidirectional or unidirectional data communication.

Communication unit 306 also may include (with or without the telemetry system and coil) a communications circuit employing a transceiver coupled to an antenna (which may be inside or external to the hermetic housing). The transceiver preferably comprises a radio frequency (RF) transceiver and is configured for bi-directional communications via the antenna with a similar transceiver circuit disposed in external patient controller 400 and/or external physician controller 500. For example, the transceiver may receive stimulation commands from external patient controller 400 and programming data from external physician controller 500. Microprocessor 302 may direct changes to electrodes included in the set of excitation electrodes used for stimulation, as well as the preferred stimulation regimes, including pulse duration, frequency of alternating current, voltage, current, and/or period of stimulation, may start or stop a stimulation session, and/or may conduct an assessment to reassess the preferred subset of electrodes, responsive to programming data and/or stimulation commands received from a corresponding transceiver and antenna of external patient controller 400 and/or external physician controller 500 via the antenna and the transceiver of communication unit 306. The transceiver also may include a low power mode of operation, such that it periodically awakens to listen for incoming messages and responds only to those messages including the unique device identifier assigned to that programmable controller. In addition, the transceiver may employ an encryption routine to ensure that messages sent from, or received by, programmable controller 300 cannot be intercepted or forged. Communication unit 306 may include a wireless chipset; e.g., WiFi, BLUETOOTH™, cellular, Zigbee, or the like; thereby enabling programmable controller 300 to communicate wirelessly with external patient controller 400 and/or external physician controller 500.

System sensors 308 may comprise one or more sensors that monitor operation of the systems of programmable controller 300, and log data relating to system operation as well as system faults, which may be stored in a log for later readout using external physician controller 500. Microprocessor 302 may be programmed to receive a sensor signal from system sensors 308 and to adjust the stimulation parameters based on the sensor signal. Sensors 308 may include, for example, a humidity sensor to measure moisture within the housing of programmable controller 300, which may provide information relating to the state of the electronic components, and/or a temperature sensor, e.g., for measuring battery temperature during charging to ensure safe operation of the battery. Data from the system sensors may be logged by microprocessor 302 and stored in non-volatile memory 304 for later transmission to external physician controller 500.

Power supply 310 powers the electrical components of programmable controller 300, and may comprise a primary cell or battery, a secondary (rechargeable) cell or battery or a combination of both. Alternatively, power supply 310 may not include a cell or battery, but instead comprise a capacitor that stores energy transmitted through the skin via a Transcutaneous Energy Transmission System (TETs), e.g., by inductive coupling. In a preferred embodiment, power supply 310 comprises a lithium ion battery.

Stimulation circuit 312 is configured to send pulses, using energy supplied from power supply 310, to electrodes 204 such that the selected electrode(s) supply electrical stimulation at the desired parameters.

Microprocessor 302 further may be coupled to demultiplexer 314 so that any subset of electrodes 204 of the arrays may be selectably coupled to stimulation circuit 312. In this way, an appropriate electrode set may be chosen from the entire selection of electrodes implanted in the patient's body to achieve a desired therapeutic effect. Demultiplexer 314 preferably operates at high speed, thereby allowing successive stimulation pulses to be applied to different electrode combinations.

Figure 6:
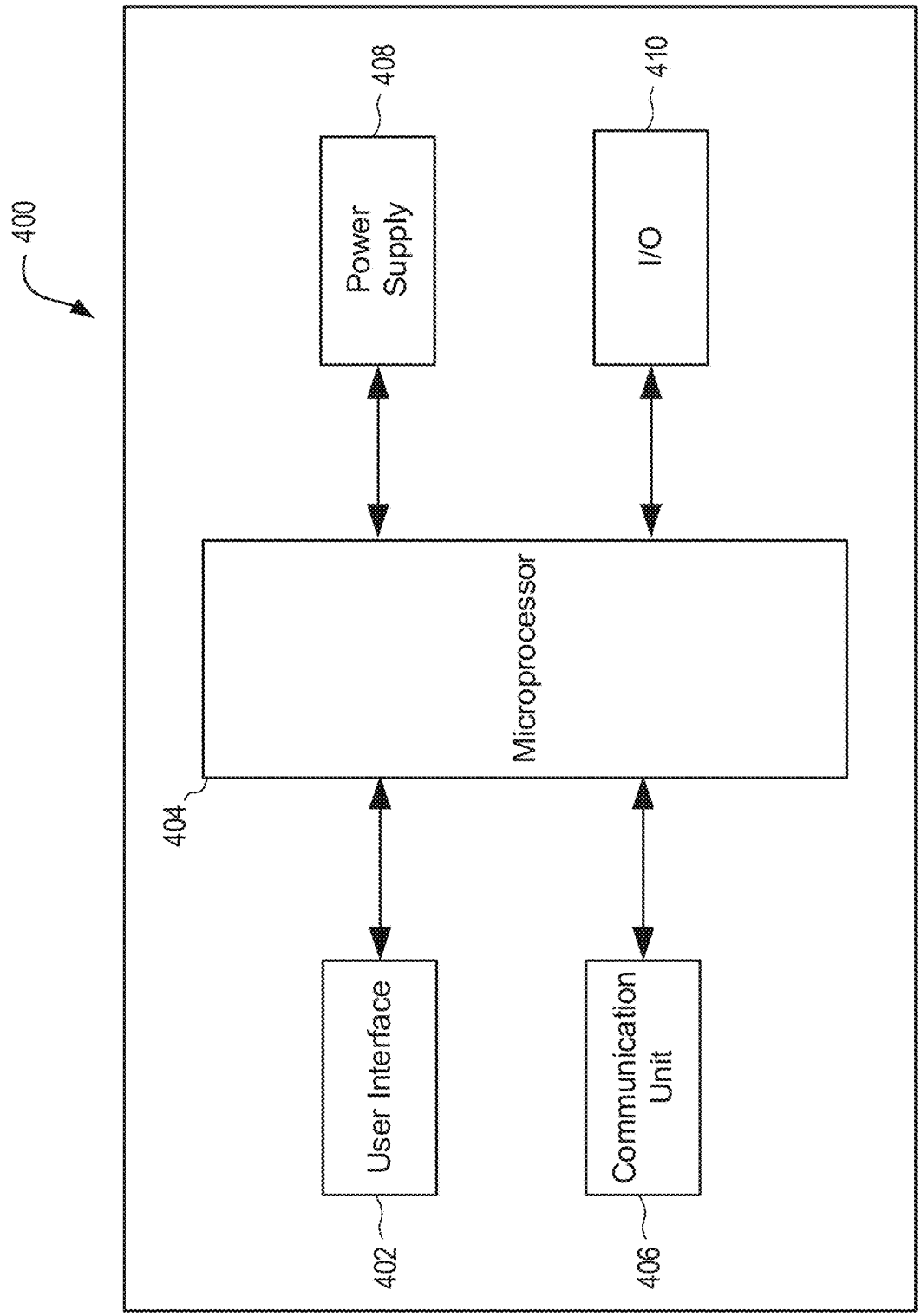
FIG. 6 depicts a generalized block diagram of an exemplary external patient controller of the stimulation system of FIG. 1.

With respect to FIG. 6, a generalized schematic diagram of the internal functional components of external patient controller 400 is now described. External patient controller 400 may include user interface 402, programmable microprocessor 404, communication unit 406, power supply 408, and input and output circuitry (I/O) 410. As explained above, external patient controller 400 may be specifically designed for use with implantable stimulation unit 200 or alternatively may be a multipurpose smartphone, laptop, tablet, smartwatch, or the like programmed to communicate with implantable stimulation unit 200 and/or external physician controller 500. In the latter case, user interface 402, programmable microprocessor 404, communication unit 406, power supply 408, and I/O 410 may be hardware previously installed on the smartphone, laptop, tablet, smartwatch, or the like.

Microprocessor 404 is electrically coupled to, and configured to control, the internal functional components of external patient controller 400. Microprocessor 404 may comprise a commercially available microcontroller unit including a programmable microprocessor, volatile memory, nonvolatile memory such as EEPROM for storing programming and nonvolatile storage, e.g., Flash memory, for storing firmware and a log of system operational parameters and patient data. The memory of microprocessor 404 may store program instructions that, when executed by the processor of microprocessor 404, cause the processor and the functional components of external patient controller 400 to provide the functionality ascribed to them herein. Preferably, microprocessor 404 is programmable, and is programmed to store changes to electrodes included in the set of excitation electrodes used for stimulation, as well as the preferred stimulation regimes, including, pulse duration, frequency of alternating current, voltage, current, and/or period of stimulation, responsive to user input received at user interface 402 and/or at an external physician controller 500 and send stimulation commands and programming data to programmable controller 300 via communication unit 406.

Microprocessor 404 may be coupled to communication unit 406, which may communicate with programmable controller 300 and external physician controller 500. Communication unit 406 may include an inductive unit having a telemetry system and coil and/or a RF unit having a transceiver and antenna with a wireless chipset; e.g., WiFi, BLUETOOTH™, cellular, Zigbee, or the like; thereby enabling external patient controller 400 to communicate wirelessly with programmable controller 300 and/or external physician controller 500 and to optionally supply power to programmable controller 300.

User interface 402 receives user input and displays information to the user. User interface 402 may include buttons, LEDs, a display, a touch screen, a keypad, a microphone, a speaker, a trackball, or the like for receiving user input and/or displaying information to the user. For example, user interface 402 may display current stimulation parameters and permit a user to adjust the stimulation parameters. In a preferred embodiment, a limited number of stimulation parameters may be adjusted at user interface 402 to lessen the chance of injury caused by adjustments made by non-physician users. For example, user interface 402 may only permit a user to start or stop a stimulation session using excitation electrodes, such as a first stimulation pulse sequence corresponding to a first mode for invoking a rapid erectile response, a second nerve rehabilitation stimulation mode selected to rehabilitate neural transmission in a cavernous nerve, or a third penile rehabilitation mode selected to reduce penile fibrosis.

Power supply 408 powers the electrical components of external patient controller 400, and may comprise a primary cell or battery, a secondary (rechargeable) cell or battery or a combination of both. Alternatively, power supply 408 may be a port to allow external patient controller 400 to be plugged into a conventional wall socket for powering components.

Input and output circuitry (I/O) 410 may include ports for data communication such as wired communication with a computer and/or ports for receiving removable memory, e.g., SD card, upon which program instructions or data related to external patient controller 400 use may be stored.

Figure 7:
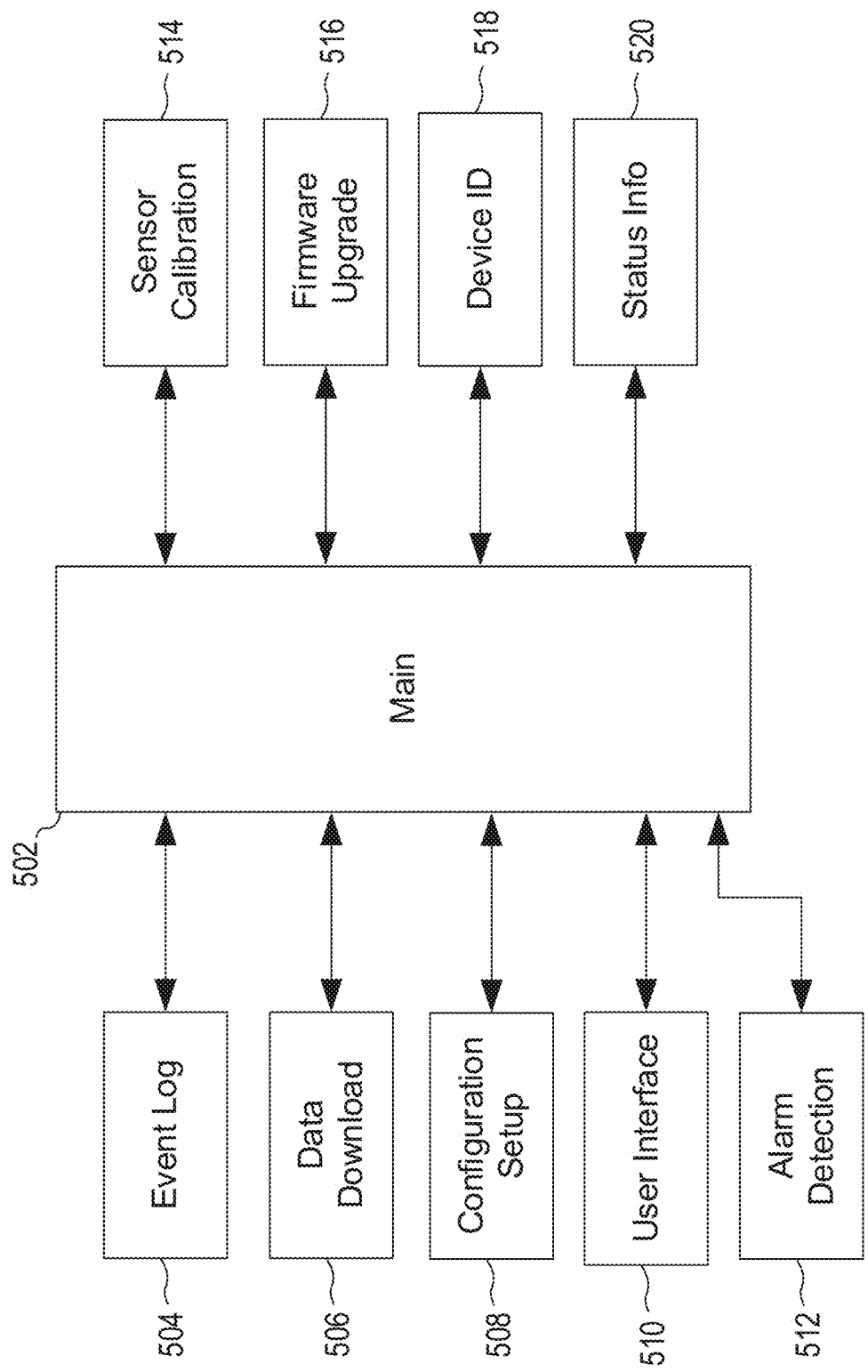
FIG. 7 is a block diagram of the functional components of an exemplary software-based programming system configured to run on the external physician controller of the stimulation system of FIG. 1.

Referring to FIG. 7, the software implemented on external physician controller 500 is now described. The software comprises a number of functional blocks, schematically depicted in FIG. 7, including main block 502, event logging block 504, data download block 506, configuration setup block 508, user interface block 510, alarm detection block 512, sensor calibration block 514, firmware upgrade block 516, device identifier block 518, and status information block 520. The software preferably is written in C++ and employs an object oriented format. In one preferred embodiment, the software is configured to run on top of a Microsoft Windows® (a registered trademark of Microsoft Corporation, Redmond, Wash.) or Unix-based operating system, such as are conventionally employed on desktop and laptop computers. As discussed above, the computer may include a transceiver, an antenna, and a wireless card; e.g., conforming to the IEEE 802.11 standard, cellular, BLUETOOTH™, Zigbee, or the like; thereby enabling programmable controller 300 and/or external patient controller 400 to communicate wirelessly with external physician controller 500.

Main block 502 preferably includes a main software routine that executes on the physician's computer, and controls overall operation of the other functional blocks. Main block 502 enables the physician to download event data and alarm information stored on programmable controller 300 and/or external patient controller 400, to his office computer, and also permits external physician controller 500 to directly control operation of programmable controller 300. Main block 502 also enables the physician to upload firmware updates and configuration data to programmable controller 300.

Event Log block 504 is a record of operational data downloaded from programmable controller 300 and may include, for example, treatment session start and stop times, current stimulation parameters, stimulation parameters from previous treatment sessions, sensor data, battery current, battery voltage, battery status, and the like. The event log also may include the occurrence of events, such as alarms or other abnormal conditions.

Data Download block 506 is a routine that commands programmable controller 300, to transfer data to external physician controller 500 for download after programmable controller 300 is coupled to external physician controller 500. Data Download block 506 may initiate, either automatically or at the instigation of the physician via user interface block 510, downloading of data stored in the event log.

Configuration Setup block 508 is a routine that configures the parameters stored within programmable controller 300 that control operation of programmable controller 300. The interval timing parameters may determine, e.g., how long the processor remains in sleep mode prior to being awakened to listen for radio communications or to control programmable controller 300 operation. The interval timing parameters may control, for example, the duration of a stimulation session. Interval timing settings transmitted to programmable controller 300 also may determine when and how often event data is written to the memory in microprocessor 302. In an embodiment in which external physician controller 500 is also configured to transfer data to external patient controller 400, external physician controller 500 also may be used to configure timing parameters used by the firmware executed by microprocessor 404 of external patient controller 400. Block 508 also may be used by the physician to configure parameters stored within the memory of microprocessor 302 relating to limit values on operation of microprocessor 302. These values may include times when programmable controller 300 may and may not operate, etc.

Block 508 also may configure parameters stored within the memory of microprocessor 302 relating to control of operation of programmable controller 300. These values may include stimulation parameters.

User interface block 510 handles display of information retrieved from programmable controller 300 and/or external patient controller 400 and data download block 506, and presents that information in an intuitive, easily understood format for physician review. Such information may include status of programmable controller 300, treatment session start and stop times, current stimulation parameters, stimulation parameters from previous treatment sessions, sensor data, battery status, and the like. User interface block 510 also generates user interface screens that permit the physician to input information to configure the session timing, stimulation parameters, and requests to determine or re-determine the subset excitation electrodes, etc.

Alarm detection block 512 may include a routine for evaluating the data retrieved from programmable controller 300 and flagging abnormal conditions for the physician's attention. For example, alarm detection block 512 may flag when a parameter measured by system sensors 308 is above or below a predetermined threshold.

Sensor calibration block 514 may include a routines for testing or measuring drift, of system sensors 308 employed in programmable controller 300, e.g., due to aging or change in humidity. Block 514 may then compute offset values for correcting measured data from the sensors, and transmit that information to programmable controller 300 for storage in the nonvolatile memory of microprocessor 302.

Firmware upgrade block 516 may comprise a routine for checking the version numbers of the controller firmware installed on programmable controller 300 and/or external patient controller 400 and identify whether upgraded firmware exists. If so, the routine may notify the physician and permit the physician to download revised firmware to programmable controller 300 and/or external patient controller 400, in nonvolatile memory.

Device identifier block 518 may include a unique identifier for programmable controller 300 that is stored in nonvolatile memory 304 of microprocessor 302 and a routine for reading that data when external physician controller 500 is coupled to programmable controller 300. The device identifier also may be used by programmable controller 300 to confirm that communications received from external patient controller 400 and/or external physician controller 500 are intended for that specific programmable controller. Likewise, this information is employed by external patient controller 400 and/or external physician controller 500 to determine whether a received message was generated by the programmable controller associated with that system. Finally, the device identifier information may be employed by external physician controller 500 to confirm that external patient controller 400 and programmable controller 300 constitute a matched set.

Status information block 520 comprises a routine for interrogating programmable controller 300 to retrieve current status data from programmable controller 300. Such information may include, for example, battery status, stimulation parameters, the date and time on the internal clocks of treatment sessions, version control information for the firmware and hardware currently in use, and sensor data.

Figure 8A:
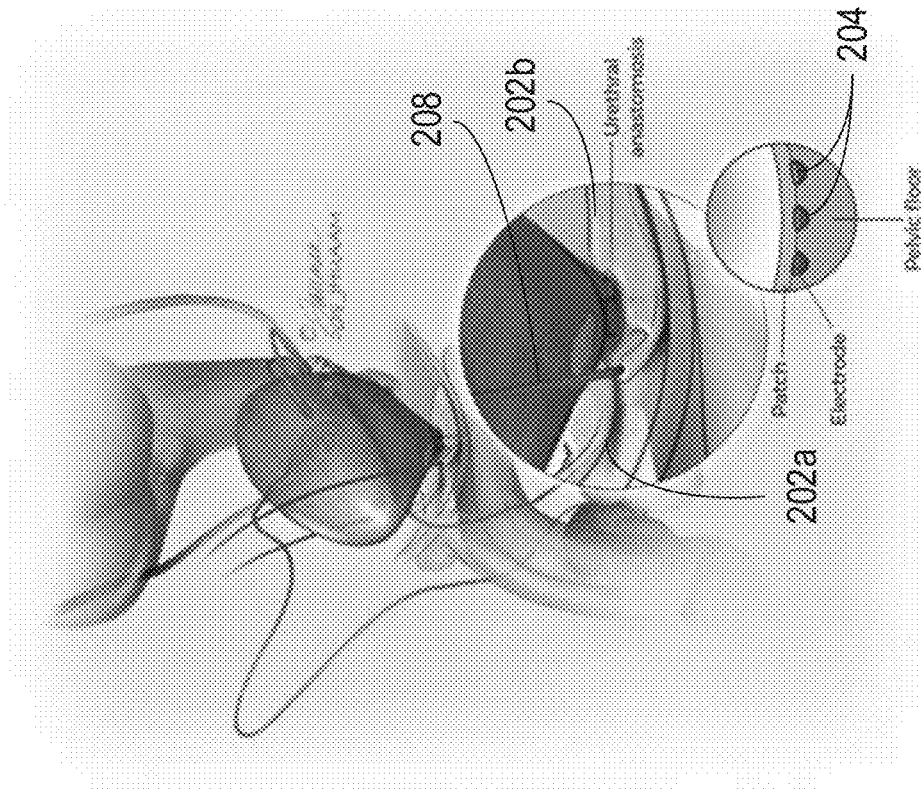
FIGS. 8A and 8B are, respectively, perspective with inset detail views showing placement of the flexible paddles of FIG. 2 positioned on a patient's prostate and pelvic plexus
Figure 8B:
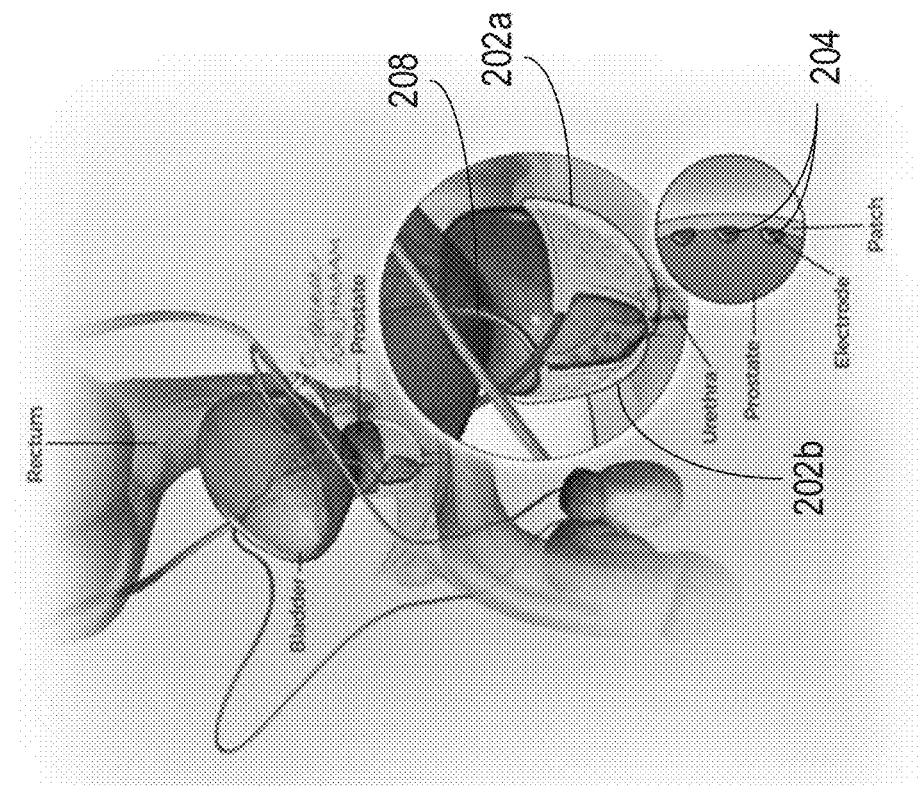

FIGS. 8A and 8B illustrate positioning of the flexible paddles 202*a* and 202*b* on the prostate and pelvic plexus, respectively. As described above with respect to FIGS. 2A and 2B, each of flexible paddles 202*a* and 202*b* carries an array of electrodes 204 and suture holes 206 and is coupled to programmable controller 300 via one or more cables 208. The system may be implanted laparoscopically, for example, by folding the flexible paddles to pass them through a trocar. Insets in FIGS. 8A and 8B depict local anatomy showing the bladder, prostate, urethra, and pelvic floor. In FIG. 8A, flexible paddles 202 are shown positioned against the prostate. Alternatively, flexible paddles 202 may be positioned against the pelvic plexus such that paddles 202 surround the urethra, as shown in FIG. 8B. Implantation on the pelvic plexus may be preferable for patients that have had a prostatectomy that partially or completely removed the prostate.

Referring now to FIGS. 9A and 9B, positioning of the flexible paddles 202 is described. As described above with respect to FIGS. 2A and 2B, each flexible paddle 202 preferably has a substantially hemispherical shape, with protruding portion 203 extending from the corner of the flexible paddle farthest from cable 208. First flexible paddle 202*a* and second flexible paddle 202*b* may be positioned such that the side of the flexible paddles with exposed electrodes contacts the pelvic plexus and the flexible paddles surround the urethra and protruding portions 203 face each other. Flexible paddles 202 include suture holes 206 through which a suture may anchor the flexible paddle to the pelvic plexus. In FIG. 9A, a first position is illustrated such that protruding portions 203 of the paddles are proximate to each other. In FIG. 9B, a second position is shown in which protruding portions 203 of the paddles are farther away from each other, which may be advantageous if a patient's cavernous nerves are located farther away from the urethra.

Programmable controller 300, which is operatively coupled to the arrays of electrodes, may be programmed to selectively activate electrodes 204 during implantation of the paddles to determine the optimal position, e.g., a first position or a second position as shown in FIGS. 9A and 9B, to implant the flexible paddles. For example, a flexible paddle may be placed at a first position adjacent to the pelvic plexus and near at least one cavernous nerve (e.g., FIG. 9A). The programmable controller then may cause the stimulator circuit to activate electrodes 204 at the first position to generate a first positional response. Activation of the cavernous nerves may be measured, for example, using a penile plethysmograph to measure penile diameter or circumference variation and penile tumescence. The flexible paddle then may be moved to a second position, different from the first position, adjacent to the pelvic plexus and near at least one cavernous nerve (e.g., FIG. 9B). The programmable controller again may selectively activate electrodes 204 at the second position to generate a second positional response. The programmable controller also may compare the first and second positional responses to determine the position that elicits an erectile response via feedback from sensor systems 308 or responsive to input from external patient controller 400 or external physician controller 500. If more than one position elicits an erectile response, the position that elicits the strongest or most rapid erectile response without causing significant discomfort or side effects, may be selected as the preferred paddle placement position.

Referring now to FIGS. 10A to 10C, a process of assessing tissue stimulation with sequentially varied directions of current flow within an array of electrodes 204 is described. As explained above, each of electrodes 204 on flexible paddles 202*a* and 202*b* may be individually accessed to serve as a source or a sink to permit current flow in multiple directions, as indicated by the arrows between electrodes 204 in FIGS. 10A to 10C. In FIG. 10A, a first direction of current flow is indicated by arrows 220*a* in a diagonal direction towards the other flexible paddle. For example, current flows from electrode 1 to electrode 2, but not between electrode 1 and electrodes 3 or 4. FIG. 10B shows second direction of current flow 220*b* in which current flows between electrodes 204 in each flexible paddle in a diagonal direction away from the other flexible paddle. As depicted in FIG. 10B, current flows from electrode 1 to electrode 3, but not between electrode 1 and electrodes 2 or 4. FIG. 10C shows third direction of current flow 220*c*, in which current flows between electrodes 204 in each flexible paddle in a downward direction. For example, current may flow from electrode 1 to electrode 4, but not from electrode 1 to electrodes 2 or 3. As will be understood by a person having ordinary skill in the art, depending on the number and arrangement of the array of electrodes 204, the directions of current flow may be different from that shown in FIGS. 10A-10C.

With respect to FIGS. 11A to 11C, grouping of electrodes 204 into exemplary regions is described. FIGS. 11A to 11C correspond to the current flow directions depicted in FIGS. 10A to 10C, respectively. Each array of electrodes 204, for example a first array and a second array, has at least two predetermined regions of electrodes 222. For example, first region of electrodes 222*a* and second region of electrodes 222*b* may be disposed on a first flexible paddle and third region of electrodes 222*c* and fourth region of electrodes 222*d* may be disposed on a second flexible paddle. As will be understood by a person having ordinary skill in the art, each paddle may have more than two regions of electrodes and the regions of electrodes may be varied to include a different subset of electrode pairs. The number and composition of electrodes 204 that are included in each region may depend on the direction of current flow. For example, first region of electrodes 222a in FIG. 11A may include electrodes 1-5 while first region of electrodes 222a in FIG. 11B may include electrodes 1-4 and 6 and first region of electrodes 222a in FIG. 11C may include electrodes 1, 3, 4, 6, 7, 10 and 11.

Referring now to FIGS. 12A to 12C, selection of preferred electrode pairs within the arrays of electrodes are shown. Each of FIGS. 12A to 12C correspond to the directional current flows depicted in FIGS. 10A to 10C, respectively, and the regions of electrodes depicted in FIGS. 11A to 11C, respectively. Each array of electrodes 204 has at least one electrode pair within each region of electrodes 222, with each electrode pair including two electrodes 204 from the array of electrodes. Each region of electrodes 222 may have the same or a different number of electrodes 204 and electrode pairs as the other regions of electrodes 222.

Figure 13:
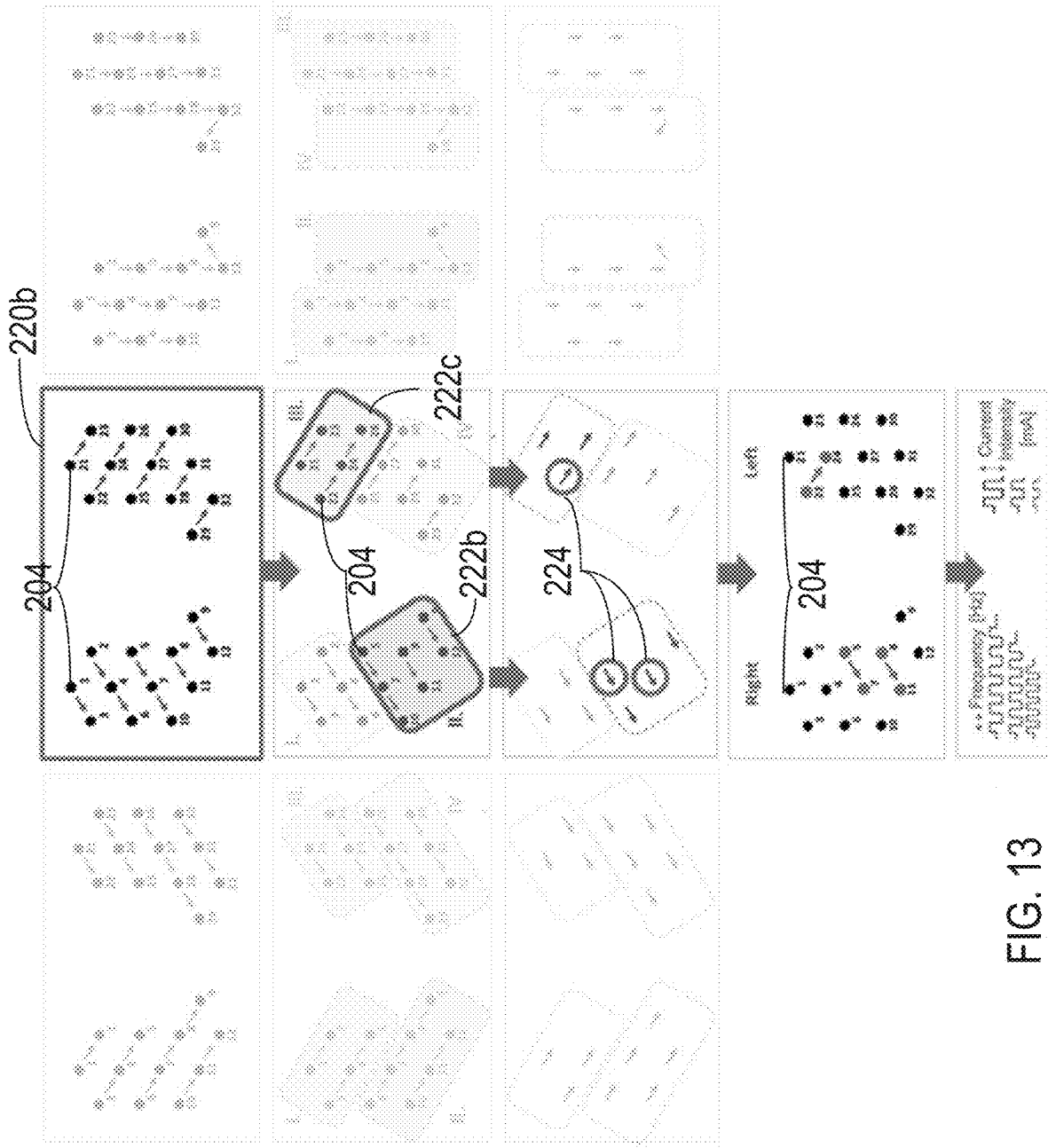
FIG. 13 depicts an exemplary method of defining preferred excitation electrodes and regions for use in electroneurostimulation to obtain sexual arousal.

Referring to FIG. 13, a programmed method for identifying a subset of excitation electrodes is described, in which a preferred direction of current flow, region of electrodes, and preferred electrode pairs are determined. Following that electrode selection process, a programmed method of determining parameters for preferred stimulation regimes to elicit favorable erectile response is completed. In accordance with one aspect of the present invention, programmable controller 300 is operatively coupled to the arrays of electrodes and programmed to selectively activate electrodes 204 to determine the excitation electrodes and preferred stimulation regimes.

More specifically, programmable controller 300 is programmed to selectively activate electrodes 204 within the array of electrodes in at least two directions of current flow, for example, as shown in FIGS. 10A to 10C. Sequential stimulation may be applied between each electrode pair on the array of electrodes and an erectile response may be measured. To determine the erectile response, activation of the cavernous nerves may be measured, for example, using a penile plethysmograph to measure penile diameter or circumference variation and penile tumescence. For each array of electrodes, the direction of current flow that elicits an erectile response may be selected as the preferred direction of current flow. If more than one direction of current flow on each array of electrodes elicits an erectile response, the direction of current flow that elicits the strongest erectile response without significant discomfort or side effects may be selected as the preferred current flow direction. For example, FIG. 13 shows that second direction of current flow 220b is selected as the preferred direction of current flow for each array of electrodes. As will be understood by a person having ordinary skill in the art, the preferred direction of current flow on the first flexible paddle may be the same or different from the preferred direction of current flow on the second flexible paddle.

Programmable controller 300 further may be programmed to selectively activate electrodes 204 within the array of electrodes, by region, using the preferred current flow direction from the preceding process. For example, if second direction of current flow 220b is the preferred current flow direction, then the regions of electrodes corresponding to the preferred current flow direction may be activated, as illustrated in FIG. 11B. Sequential stimulation may be applied between each electrode pair on each array of electrodes in the preferred current flow direction in each region and an erectile response again measured for each regional stimulation using the same method as described above. For each array of electrodes, the region of electrodes that elicits an erectile response may be selected as a preferred electrode region. If more than one region of electrodes elicits an erectile response, the region of electrodes that elicits the strongest erectile response without causing significant discomfort or side effects is selected as the preferred region. For example, FIG. 13 depicts second region of electrodes 222b on a first flexible paddle and third region of electrodes 222c on a second flexible paddle being selected as the preferred regions.

Next, programmable controller 300 selectively activates electrodes 204 within the array of electrodes in the preferred current flow direction and preferred regions. For example, FIG. 13 depicts that second direction of current flow 220b is the preferred current flow direction and second region of electrodes 222b on the first flexible paddle and third region of electrodes 222c on the second flexible paddle are the preferred regions. Sequential stimulation may be applied between each electrode pair on the array of electrodes in the preferred direction of current flow and in the preferred regions and an erectile response may be measured using the same method described above. For each array of electrodes, the one or more electrode pairs that elicits an erectile response may be selected as a preferred electrode pair. If more than one electrode pair elicits an erectile response, the one or more electrode pairs that elicits the strongest erectile response without causing significant discomfort or side effects may be selected as the preferred electrode pair(s). In FIG. 13, three preferred electrode pairs 224 are identified as the subset of excitation electrodes. As will be understood by a person having ordinary skill in the art, the number of preferred electrode pairs on the first flexible paddle may be the same or different from the number of preferred electrode pairs on the second flexible paddle.

After the preferred electrode pairs 224 are determined, multiple stimulation parameters having a unique combination of frequency and intensity amplitude may be applied to the preferred electrode pairs. Stimulation pulse sequences for different uses may be determined by comparing the responses generated by activating the preferred electrode pairs at different modes having different stimulation parameters. For example, a stimulation pulse sequence corresponding to a mode of activation for an erection may be determined. The stimulation regime for producing an erection may apply current amplitude in the range of 0.5 to 25 mA, frequency in the range of 10 to 48 Hz, pulse width in the range of 0.1 to 1 milliseconds. Alternatively, or in addition, the device may be used to rehabilitate at least one cavernous nerve and to determine a nerve rehabilitation stimulation regime corresponding to a mode of activation for nerve rehabilitation. The nerve rehabilitation stimulation regime may comprise stimulation parameters with a lower current intensity than the stimulation regime for producing an erection. For example, the nerve rehabilitation stimulation regime may apply current amplitude in the range of 0.1 to 2 mA, frequency in the range of 10 to 48 Hz, and pulse width in the range of 0.01 to 1 milliseconds. The nerve rehabilitation stimulation regime may be programmed to automatically execute at least once per day.

Alternatively, the device may be used to determine a penile rehabilitation stimulation regime, corresponding to a mode of activation for penile rehabilitation. After a prostatectomy, if the cavernous nerves are injured or completely severed, the penile rehabilitation stimulation regime may be used to induce at least partial penile tumescence to increase tissue oxygenation and maintain penile function, thereby reducing penile fibrosis. Such stimulation regime may be executed at least once per day while the cavernous nerves reestablish naturally, or with assistance from the nerve rehabilitation stimulation regime, reconnect and regenerate. The penile rehabilitation stimulation regime may comprise stimulation parameters with a higher current intensity than the nerve rehabilitation stimulation regime and a lower current intensity than the stimulation regime for producing an erection. For example, the penile rehabilitation stimulation regime may apply current amplitude in the range of 0.5 to 25 mA, frequency in the range of 10 to 48 Hz, pulse width in the range of 0.1 to 1 milliseconds. The penile rehabilitation stimulation regime may be programmed to automatically execute at least once per day, and such actuation may occur at a different time than the nerve rehabilitation program.

The preferred direction of current flow, electrode regions, electrode pairs, and stimulation parameters may be stored in the nonvolatile memory of programmable controller 300, external patient controller 400, and/or external physician controller 500. Multiple stimulation regimes may also be stored in the memory of programmable controller 300, external patient controller 400, and/or external physician controller 500 such that the programmable controller may be selectively activated in response to patient or physician input. For example, a patient may selectively activate the stimulation regime for producing an erection. Alternatively, if so programmed, the programmable controller may automatically execute the nerve rehabilitation stimulation regime and/or the penile rehabilitation stimulation regime at least once per day following a prostatectomy, preferably for one hour for each rehabilitation stimulation regime.

Figure 14:
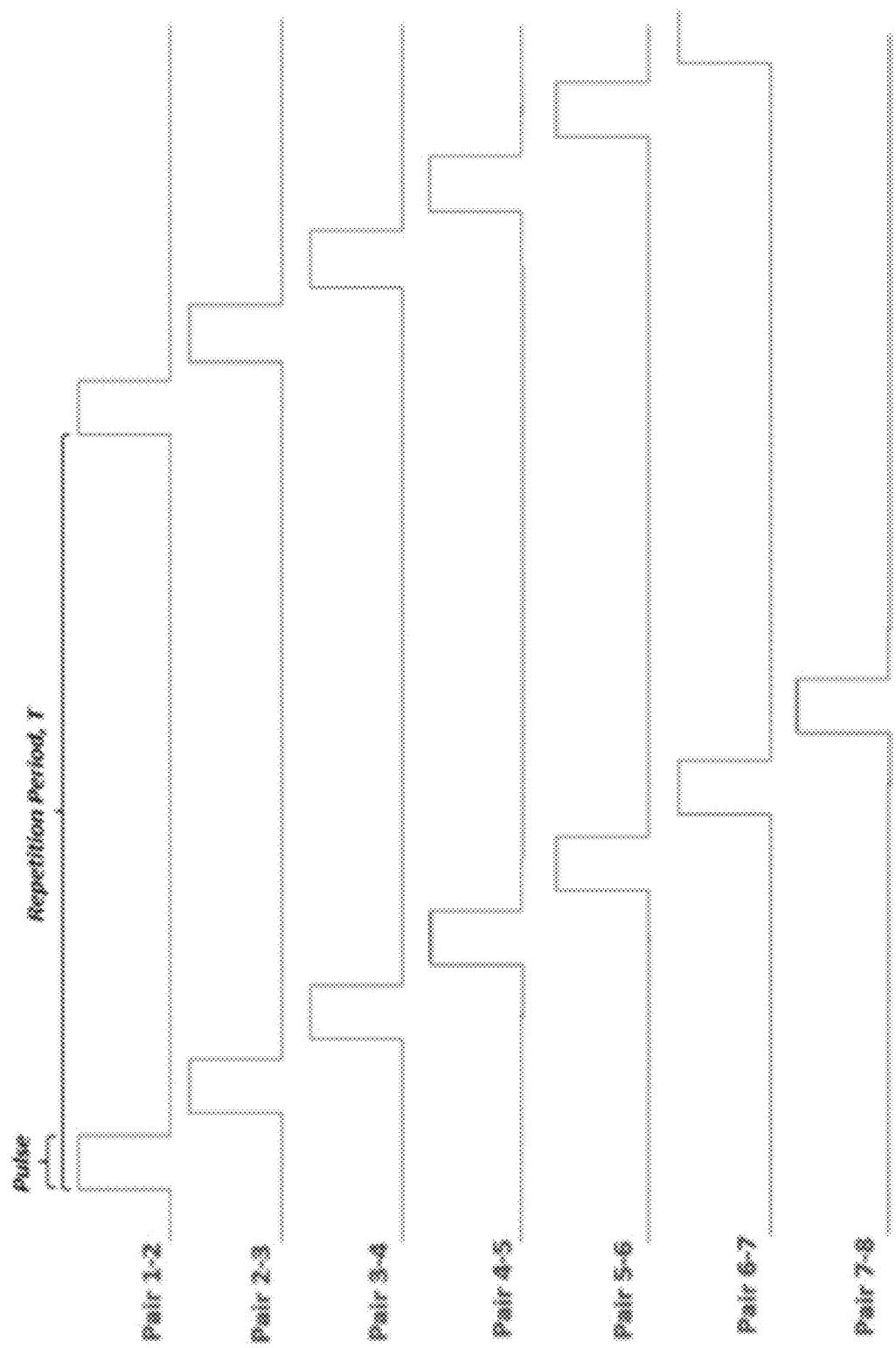
FIG. 14 depicts a method of serially intraoperatively scanning adjacent electrode pairs in accordance with the principles of the present invention.

With respect to FIG. 14, a schematic of operation of the intraoperative scanning process is described. Sequential stimulation will be applied between each electrode pair within each array of electrodes. The stimulation of each electrode pair will be applied automatically during the inter-pulse period of the other electrode pairs. The intraoperative stimulation allows the activation of cavernous nerves, which is detected by a penile plethysmograph to measure penile diameter or circumference variation and penile tumescence. During the scanning procedure, a period of 1 to 2 minutes of stimulation per configuration may be needed to allow a proper measurement. A resting period of 5 minutes between each stimulation may be allowed for stabilization, avoiding detumescence refractory effects.

Figure 15:
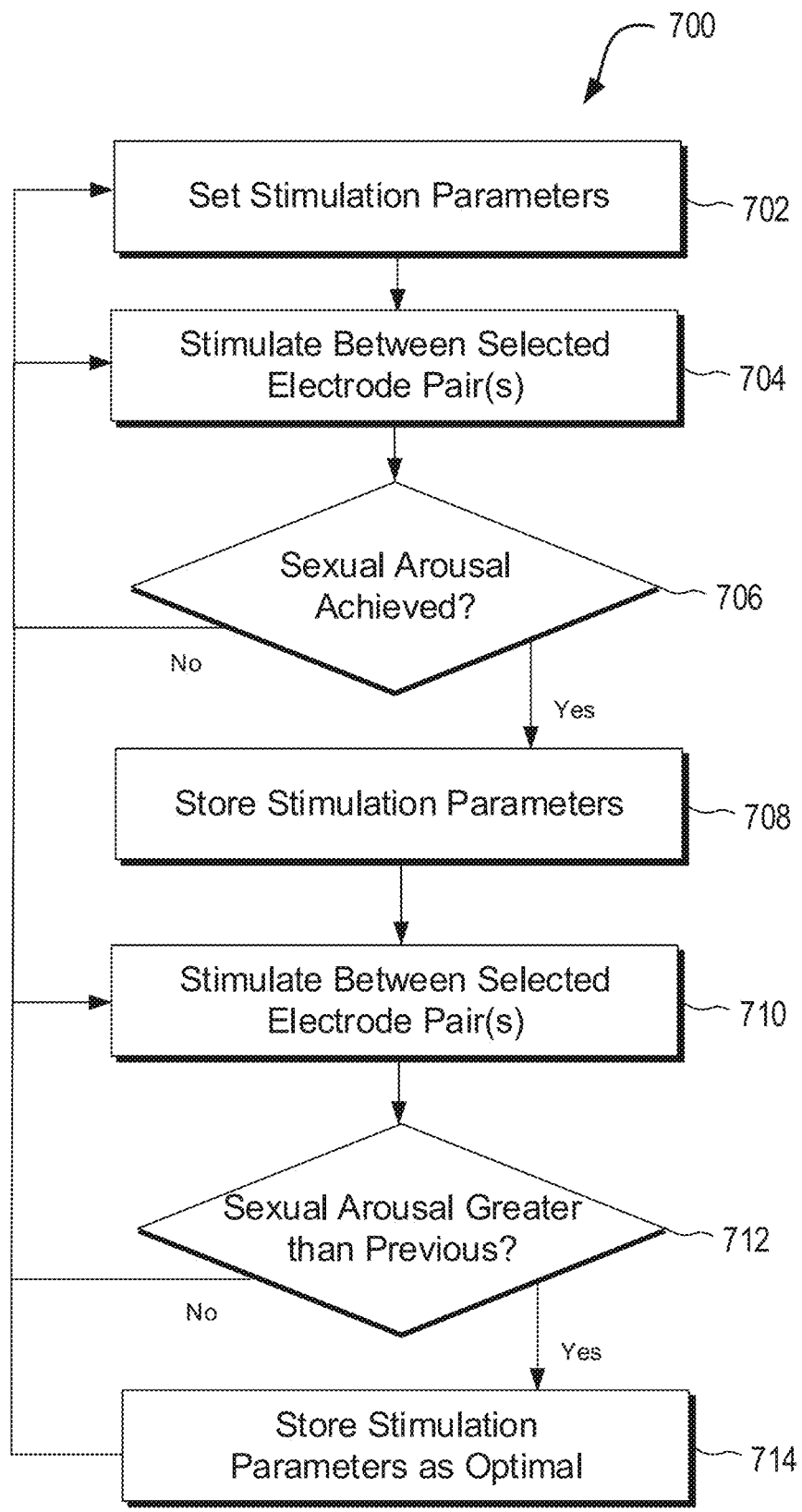
FIG. 15 is a flow chart illustrating the steps of an exemplary method for configuring a subset of an array of electrodes for stimulation to cause optimal sexual arousal in accordance with the principles of the present invention.

In FIG. 15, an exemplary method for determining a subset of the array of electrodes positioned to supply electrical stimulation to at least one cavernous nerve via the pelvic plexus to cause sexual arousal, e.g., an erection, preferably post-implantation, is described. In method 700, at 702, stimulation parameters are set which may include the pair(s) of electrodes 204 in the array to be used, pulse duration, frequency of alternating current, voltage, current, and period of stimulation. Stimulation parameters may be set at external patient controller 400, but are preferably set at external physician controller 500. At 704, electrical stimulation is supplied to tissue, e.g., pelvic plexus, between the selected electrode pair(s) of the array at the set stimulation parameters. The selected electrode pair(s) of the array at the set stimulation parameters may be selected by a physician via external physician controller 500 and/or determined as a result of the scanning protocol described above. At 706, it is observed whether sexual arousal, e.g., an erection, is achieved. If not, stimulation parameters may be reset for the selected electrode pair(s) or different electrode pair(s) may be selected for stimulation with the same parameters or at adjusted parameters. If sexual arousal is achieved, the stimulation parameters, including the electrode pair(s), are stored in memory at programmable controller 300, external patient controller 400, and/or physician controller 500.

Optionally, even after sexual arousal is achieved, further stimulation may be conducted at the electrode pair(s) using adjusted stimulation parameters or further different electrode pair(s) may be selected for stimulation with the same parameters or at adjusted parameters, at 710, to determine if stronger sexual arousal can be achieved, at 712. If not, stimulation, at 710, may be repeated with different configurations or the testing may end and the parameters stored at 708 may be used. If stronger sexual arousal is achieved, the stimulation parameters, including the electrode pair(s), are stored in memory at programmable controller 300, external patient controller 400, and/or physician controller 500 as the preferred parameters and the previously stored parameters at 708 may be overwritten. Optionally, even after stronger sexual arousal is achieved, further stimulation may be conducted at the electrode pair(s) using adjusted stimulation parameters or further different electrode pair(s) may be selected for stimulation with the same parameters or at adjusted parameters, at 710, to determine if even stronger sexual arousal can be achieved, at 712.

Once the user is satisfied that preferred parameters have been determined, either because all electrode pairings in the array were tested or because suitable sexual arousal was achieved, the preferred parameters are stored. In this manner, a stimulation routine at the preferred parameters may be initiated by patient external controller 400 and/or external physician controller 500 at a later time; e.g., minutes, hours, days, months, years later; to cause sexual arousal, e.g., an erection.

Figure 16:
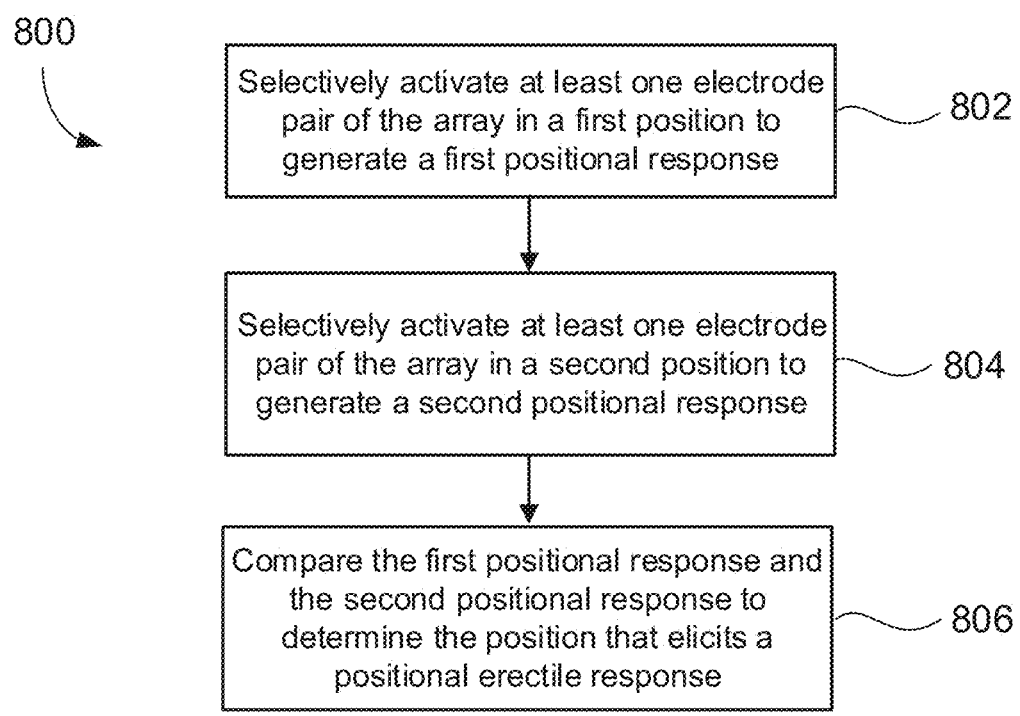
FIG. 16 is a flow chart illustrating the steps of an exemplary method for determining the optimal position to implant the flexible paddles in accordance with the principles of the present disclosure.

Referring now to FIG. 16, an exemplary method for determining optimal positioning for the flexible paddles is described. In method 800, at step 802, the array of electrodes is placed at a first position adjacent to the pelvic plexus and near at least one cavernous nerve. At least one pair of electrodes is selectively activated to stimulate at least one cavernous nerve and to generate a first positional response. At step 804, the same process is repeated at a second position, different from the first position, adjacent to the pelvic plexus and near at least one cavernous nerve. Specifically, at least one electrode pair is selectively activated to stimulate at least one cavernous nerve and to generate a second positional response. At step 806, the first position response and the second positional response are compared to determine which response elicits a stronger positional erectile response. If more than one position elicits an erectile response, the position that elicits the strongest erectile response without causing significant discomfort or side effects may be selected as the optimal position. The process may be repeated at a third position to further determine the optimal position to implant the flexible paddle.

Figure 17:
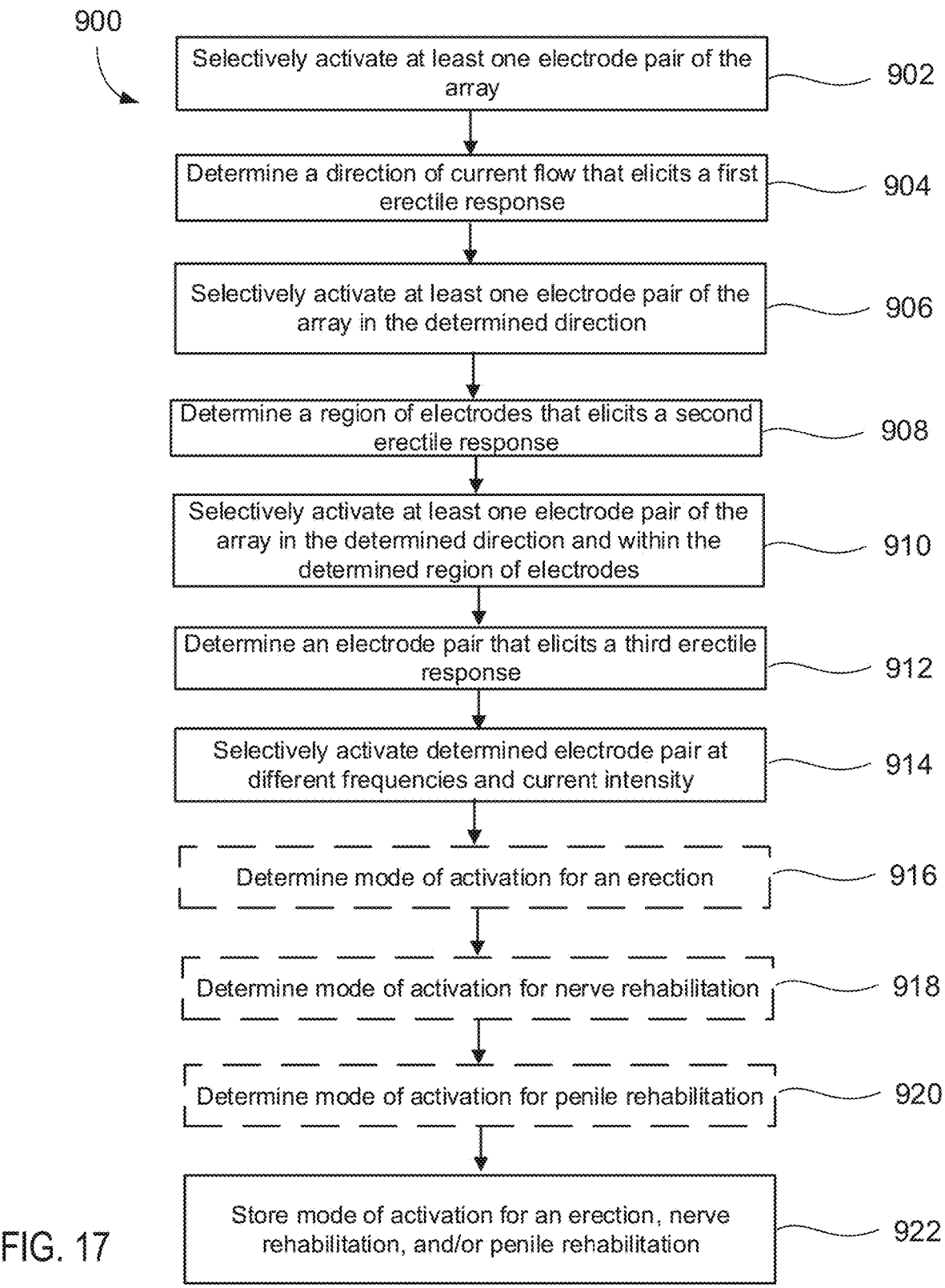
FIG. 17 is a flow chart illustrating the steps of an exemplary method for determining the optimal stimulation regime to cause an erection, the stimulation regime for rehabilitation of at least one cavernous nerve, and/or the stimulation regime for penile rehabilitation to reduce penile fibrosis.

Referring now to FIG. 17, an exemplary method for determining a preferred stimulation regime to cause an erection, and optionally, a preferred stimulation regime for neural rehabilitation, and/or for penile rehabilitation is described. In method 900, at step 902, at least one electrode pair of the array is selectively activated to stimulate at least one cavernous nerve. At least one electrode pair may be selectively activated in a first direction and a second direction to generate a first directional response and a second directional response, respectively. At step 904, the direction of current flow that elicits a first erectile response may be determined by comparing the first and second directional responses. At step 906, at least one electrode pair of the array is selectively activated in the preferred direction to stimulate at least one cavernous nerve. At least one electrode pair in a first region and at least one electrode pair in a second region may be selectively activated in the preferred direction to generate a first regional response and a second regional response, respectively.

At step 908, the region of electrodes that elicits a second erectile response may be determined by comparing the first regional response and the second regional response. The process then is repeated to determine the preferred electrode pairs. At step 910, at least one electrode pair of the array is selectively activated in the preferred direction and within the preferred region. A first electrode pair and a second electrode pair within the preferred region may be selectively activated in the preferred direction to generate a first pair response and a second pair response, respectively. At step 912, one or more electrode pairs that elicits a third erectile response may be determined by comparing the first pair response and the second pair response.

At step 914, the preferred electrode pair(s) may be selectively activated at different frequencies and current intensities. The preferred electrode pair(s) may be selectively activated at a first mode having a first simulation regime and at a second mode having second stimulation regime, which employs different stimulation parameters from the first stimulation regime, to generate a first response and a second response. Optionally, at step 916, a mode of activation for an erection may be determined by comparing the first mode response and the second mode response. Optionally, at step 918, the comparison may be repeated to determine a mode of activation for rehabilitation of at least one cavernous nerve. Optionally, at step 920, the comparison may be repeated to determine a mode of activation for penile rehabilitation, to reduce penile fibrosis. At step 922, the determined mode(s) of activation may be stored in memory of programmable controller 300, external patient controller 400, and/or physician controller 500.

Figure 18:
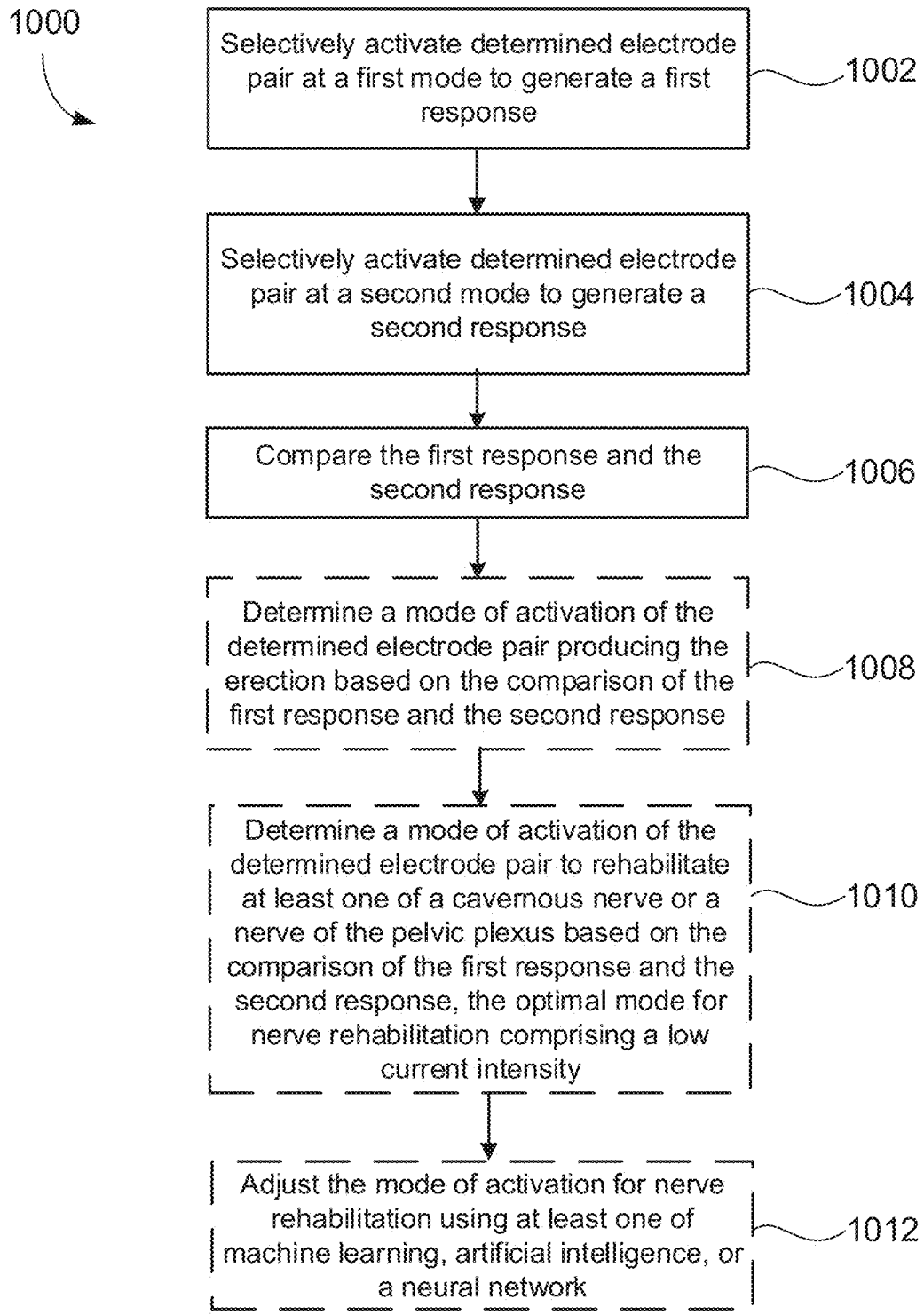
FIG. 18 is a flow chart illustrating the steps of an exemplary method for adjusting the optimal mode for rehabilitation after an interval post-implantation.

Referring now to FIG. 18, an exemplary method for adjusting a preferred mode having a stimulation regime for rehabilitation of neural transmission in a cavernous nerve is described. In method 1000, steps 1002-1010 are similar to steps 914-918 in method 900. At step 1002, the preferred electrode pairs may be selectively activated at a first mode having a first stimulation regime to generate a first response. At step 1004, the preferred electrode pairs may be selectively activated at a second mode having a second stimulation regime to generate a second response. At step 1006, the first and second responses may be compared. Optionally, at step 1008, a rapid erection mode of activation may be determined based on the comparison. Optionally, at step 1010, a mode of activation to promote rehabilitation of at least one cavernous nerve based on the comparison. The nerve rehabilitation mode may supply lower current intensity stimulation than the rapid erection mode of activation. Optionally, at step 1012, the nerve rehabilitation mode of activation may be adjusted using machine learning or other kind of artificial intelligence. In addition, the preferred electrodes also may be used to measure neural activity and those measurements may be used in conjunction with artificial intelligence to adjust the rehabilitation mode of activation to enable more efficient or effective neural transmission. Alternatively, the method of FIG. 18 may be used to adjust the stimulation regime for producing an erection or the penile rehabilitation stimulation regime for reducing fibrosis.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. An implantable system for reducing penile fibrosis following prostatectomy, the system comprising:
   a flexible paddle having an array of electrodes configured to be disposed adjacent to a patient's pelvic plexus; and
   a programmable controller comprising a stimulation circuit, a microprocessor and a memory, the stimulation circuit operatively coupled to the array, the microprocessor configured to execute programmed instructions stored in the memory to cause the stimulation circuit to selectively activate a set of excitation electrodes within the array of electrodes to stimulate one or more nerves of the patient's pelvic plexus to induce at least partial penile tumescence,
   wherein the programmed instructions:
      cause activation of the stimulation circuit at least once daily during a recuperation period following prostatectomy to reduce a risk of penile fibrosis;
      cause the stimulation circuit to excite the set of excitation electrodes with a series of stimulation parameters to identify a preferred set of stimulation parameters for inducing penile tumescence; and
      cause storage as the preferred set of stimulation parameters the set of stimulation parameters that generates a highest degree of penile tumescence, and
   wherein the programmable controller is coupled to a sensor that monitors a degree of penile tumescence.

2. The implantable system of claim 1, wherein the programmed instructions identify the preferred set of stimulation parameters responsive to input provided by an external patient controller or an external physician controller.

3. The implantable system of claim 1, wherein the stimulation circuit applies a current amplitude in a range of 0.5 to 25 mA at a frequency between 10 to 48 Hz with a pulse width between 0.1 to 1.0 milliseconds.

4. An implantable system for treating erectile dysfunction, the system comprising:
   a flexible paddle having an array of electrodes configured to be disposed adjacent to a patient's pelvic plexus; and
   a programmable controller comprising a stimulation circuit, a microprocessor and a memory, the stimulation circuit operatively coupled to the array, the microprocessor configured to execute programmed instructions stored in the memory to:
      cause the stimulation circuit to activate a subset of electrodes within the array in accordance with a first set of stimulation parameters to elicit an erection responsive to an "on-demand" input from an external patient controller or an external physician controller;
      activate, at least daily, the subset of electrodes within the array with a second set of stimulation parameters to elicit an erectile response that promotes penile rehabilitation responsive to a schedule input from the external patient controller or the external physician controller;
      cause the stimulation circuit to excite the subset of electrodes with a series of stimulation parameters to identify a preferred set of stimulation parameters for at least one of the first set of stimulation parameters or the second set of stimulation parameters; and cause storage as the preferred set of stimulation parameters the set of stimulation parameters that generates a highest degree of penile tumescence,
wherein the programmable controller is coupled to a sensor that monitors a degree of penile tumescence.

5. The implantable system of claim 4, wherein the programmed instructions identifies the preferred set of stimulation parameters responsive to input provided by the external patient controller or the external physician controller.

6. The implantable system of claim 4, wherein the first set of stimulation parameters and the second set of stimulation parameters apply a current amplitude in a range of 0.5 to 25 mA at a frequency between 10 to 48 Hz with a pulse width between 0.1 to 1.0 milliseconds.

7. The implantable system of claim 4, wherein the programmed instructions further cause the stimulation circuit to activate, at least daily, the subset of electrodes within the array with a third set of stimulation parameters to elicit an erectile response that promotes rehabilitation of a cavernous nerve responsive to a schedule input from the external patient controller or the external physician controller.

8. The implantable system of claim 7, wherein the third set of stimulation parameters applies a current amplitude in a range of 0.1 to 2 mA at a frequency between 10 to 48 Hz with a pulse width between 0.01 to 1.0 milliseconds.

9. A method of reducing penile fibrosis following prostatectomy, comprising:
during a prostatectomy procedure, implanting a flexible paddle having an array of electrodes adjacent to a patient's pelvic plexus;
during or after the prostatectomy procedure, coupling to the array of electrodes a programmable controller including a stimulation circuit, a microprocessor and a memory, wherein the microprocessor is configured to execute programmed instructions stored in the memory to cause the stimulation circuit to selectively activate a set of excitation electrodes within the array of electrodes;
executing the programmed instructions to:
cause the stimulation circuit to excite the set of excitation electrodes with a series of stimulation parameters to identify a preferred set of stimulation parameters for inducing penile tumescence; and
at least once daily during a recuperation period following the prostatectomy procedure, cause activation of the stimulation circuit to stimulate one or more nerves of the patient's pelvic plexus to induce at least partial penile tumescence, thereby reducing a risk of penile fibrosis;
providing a sensor coupled to the microprocessor, the sensor configured to monitor a degree of penile tumescence; and
storing as the preferred set of stimulation parameters the set of stimulation parameters that generates a greatest degree of penile tumescence.

10. The method of claim 9, wherein identifying the preferred set of stimulation parameters comprises accepting input provided by an external patient controller or an external physician controller.

11. The method of claim 9, wherein the stimulation circuit applies a current amplitude in a range of 0.5 to 25 mA at a frequency between 10 to 48 Hz with a pulse width between 0.1 to 1.0 milliseconds.

* * * * *